US006399067B1

(12) United States Patent
Goldstein

(10) Patent No.: US 6,399,067 B1
(45) Date of Patent: Jun. 4, 2002

(54) METHODS AND COMPOSITIONS FOR IMPAIRING MULTIPLICATION OF HIV-1

(75) Inventor: Gideon Goldstein, Short Hills, NJ (US)

(73) Assignee: Thymon L.L.C., Short Hills, NJ (US)

( * ) Notice: Subject to any disclaimer, the term of this patent is extended or adjusted under 35 U.S.C. 154(b) by 0 days.

(21) Appl. No.: 09/561,366

(22) Filed: Apr. 28, 2000

(51) Int. Cl.[7] ........................ A61K 39/00; A61K 39/12; A61K 45/00; A61K 38/00

(52) U.S. Cl. ................................ 424/188.1; 424/184.1; 424/185.1; 424/204.1; 424/278.1; 530/300

(58) Field of Search ........................... 424/184.1, 185.1, 424/188.1, 204.1, 278.1; 530/300

(56) References Cited

U.S. PATENT DOCUMENTS

| | | | | |
|---|---|---|---|---|
| 5,110,802 A | | 5/1992 | Cantin et al. | 514/44 |
| 5,158,877 A | | 10/1992 | Edwards et al. | 435/91 |
| 5,238,822 A | | 8/1993 | Dykes et al. | 435/69.1 |
| 5,891,994 A | | 4/1999 | Goldstein | 530/329 |
| 6,193,981 B1 | * | 2/2001 | Goldstein | 424/208.1 |

FOREIGN PATENT DOCUMENTS

| | | |
|---|---|---|
| WO | WO 87/02989 | 5/1987 |
| WO | WO 91/09958 | 7/1991 |
| WO | WO 91/10453 | 7/1991 |
| WO | WO 92/07871 | 5/1992 |
| WO | WO 92/14755 | 9/1992 |
| WO | WO 95/31999 | 11/1995 |
| WO | WO 99/02185 | 1/1999 |

OTHER PUBLICATIONS

S. Fawell et al., "Tat–Mediated Delivery of Heterologous Proteins into Cells", *Proc. Natl. Acad. Sci*, USA, 91:664–668 (Jan. 1994).

A. Cafaro et al., "Control of SHIV–89.6P–Infection of Cynomolgus Monkeys by HIV–1 Tat Protein Vaccine", *Nat. Med.*, 5(6):643–650 (Jun. 1999).

S. Calarota et al., "Cellular Cytotoxic Response Induced by DNA Vaccination in HIV–1–Infected Patients", *Lancet*, 351:1320–1325 (May 2, 1998).

S. S. Cohen et al., "Pronounced Acute Immunosuppression in vivo Mediated by HIV Tat Challenge", *Proc. Natl. Acad. Sci.*, USA, No. 96(19):10842–10847 (Sep. 1999).

A. Gringeri et al., "Safety and Immunogenicity of HIV–1 Tat Toxoid in Immunocompromised HIV–1–Infected Patients", *J. Hum. Virol.*, 1(4):293–298 (May/Jun. 1998).

E. Caselli et al., "DNA Immunization with HIV–1 tat Mutated in the trans Activation Domain Induces Humoral and Cellular Immune Response Against Wild–Type Tat", *J. Immunol.*, 162:5631–5638 (May 1, 1999).

(List continued on next page.)

*Primary Examiner*—Hankyel T. Park
*Assistant Examiner*—Stacy S. Brown
(74) *Attorney, Agent, or Firm*—Howson and Howson

(57) ABSTRACT

A composition which elicits antibodies to multiple known variants of Tat protein of HIV-1 of both the B and non-B clades contains the peptide R1-Asp-Pro-Asn-Leu-Asp-Pro-Trp-Asn-R2 SEQ ID NO: 23, and preferably an additional at least two variants of a peptide or polypeptide of the formula: R1-Asp-Pro-$Y_7$-Leu-Glu-Pro-Trp-$Z_{12}$-R2 SEQ ID NO: 8. In this composition, at least one of the two variants contains Arg at $Y_7$ and Lys at $Z_{12}$, and in at least a second of the two variants $Y_7$ is Asn and $Z_{12}$ is Asn. Vaccinal and pharmaceutical compositions can contain one or more such peptides associated with carrier proteins, associated in multiple antigenic peptides, or as part of recombinant proteins. Diagnostic compositions and uses are described for assessing the immune status of vaccinated patients.

17 Claims, 3 Drawing Sheets

OTHER PUBLICATIONS

M.C. Re et al., "Effect of Antibody to HIV–1 Tat Protein on Viral Replication in Vitro and Progression of HIV–1 Disease in Vivo", *J. Acquir. Immune Defic. Syndr. Hum. Virol.*, 10:408–416 (Dec. 1, 1995).

C. J. Li et al., "Tat Protein Induces Self–Perpetuating Permissivity for Productive HIV–1 Infection", *Proc. Natl. Acad. Sci.*, USA, 94:8116–8120 (Jul. 1997).

D. Brake et al., "Characterization of Murine Monoclonal Antibodies to the Tat Protein from Human Immunodeficiency Virus Type 1", *J. Virol.*, 64:962 (Feb. 1990).

D. Mann et al., "Endocytosis and Targeting of Exogenous HIV–1 Tat Protein", *EMBO J.*, 10(7):1733 (Jul. 1991).

L. Steinaa et al., "Antibody to HIV–1 Tat Protein Inhibits the Replication of Virus in Culture", *Arch. Virol.*, 139:263 (1994).

G. Zauli et al., "An Autocrine Loop of HIV Type–1 Tat Protein Responsible for the Improved Survival/Proliferation Capacity of Permanently Tat–Transfected Cells and Required for Optimal HIV–1 LTR Transactivating Activity", *J. Acq. Imm. Def. Syndr. Hum. Retroviol.*, 10:306 (Nov. 1, 1995).

G. Goldstein, "HIV–1 tat Protein as a Potential AIDS Vaccine", *Nature Med.*, 2(9):960 (Sep. 1996).

G. Goldstein, "Minimization of Chronic Plasma Viremia in Rhesus Macaques Immunized with Synthetic HIV–1 Peptides and Infected with a Chimeric Simian/Human Immunodeficiency Virus ($SHIV_{33}$)", *Vaccine*, 18:2789 (Jun. 15, 2000).

* cited by examiner

FIG. 3A [SEQ ID NO: 12]

DnaK (HSP70)- (Glu-Pro-Val-Asp-Pro- Arg -Leu-Glu-Pro-Trp-Lys-Gly-Ser)$_4$- (Glu-Pro-Val-Asp-Pro-Asn-Leu-Glu-Pro-Trp-Lys-Gly-Ser)$_4$ - (Glu-Pro-Val-Asp-Pro- Ser-Leu-Glu-Pro-Trp-Lys-Gly-Ser)$_4$ - (Glu-Pro-Val-Asp-Pro- Lys-Leu-Glu-Pro-Trp-Lys-Gly-Ser)$_4$ - (Lys-Gly-Leu-Gly-Ile-Ser-Tyr-Gly-Arg-Lys-Ser-Gly-Ser)$_4$

FIG. 3B [SEQ ID NO: 13]

DnaK (HSP70) - (Glu-Pro-Val-Asp-Pro- Arg -Leu-Glu-Pro-Trp-Lys-Gly-Ser)$_4$-(Glu-Pro-Val-Asp-Pro-Asn-Leu-Glu-Pro-Trp-Lys-Gly-Ser)$_4$ - (Glu-Pro-Val-Asp-Pro-Ser-Leu-Glu-Pro-Trp-Lys-Gly-Ser)$_4$ - (Glu-Pro-Val-Asp-Pro- Lys-Leu-Glu-Pro-Trp-Lys-Gly-Ser)$_4$ - (Glu-Pro-Val-Asp-Pro- Asn -Leu-Ala-Pro-Trp-Asn-Gly-Ser)$_4$- (Glu-Pro-Val-Asp-Pro-Asn-Leu-Glu-Pro-Trp-Asn-Gly-Ser)$_4$ - (Glu-Pro-Val-Asp-Pro- Ser-Leu-Glu-Pro-Trp-Asn-Gly-Ser)$_4$ - (Glu-Pro-Val-Asp-Pro- Lys-Leu-Glu-Pro-Trp-Asn-Gly-Ser)$_4$

Fig. 3C [SEQ ID NO: 14]

Diphtheria toxoid conjugated with -Cys-Gly-Ser-Lys-Gly-Leu-Gly-Ile-Ser-Tyr-Gly-Arg-Lys-amide

SEQUENCE LISTING

```
<160> NUMBER OF SEQ ID NOS: 39

<210> SEQ ID NO 1
<211> LENGTH: 9
<212> TYPE: PRT
<213> ORGANISM: Human immunodeficiency virus type 1

<400> SEQUENCE: 1

Arg Lys Lys Arg Arg Gln Arg Arg Arg
1               5


<210> SEQ ID NO 2
<211> LENGTH: 6
<212> TYPE: PRT
<213> ORGANISM: Human immunodeficiency virus type 1

<400> SEQUENCE: 2

Gly Arg Gly Asp Ser Pro
1               5
```

-continued

<210> SEQ ID NO 3
<211> LENGTH: 6
<212> TYPE: PRT
<213> ORGANISM: Human immunodeficiency virus type 1
<220> FEATURE:
<221> NAME/KEY: MOD_RES
<222> LOCATION: (3)..(3)
<223> OTHER INFORMATION: Xaa can be Arg, Lys , Ser or Asn

<400> SEQUENCE: 3

Asp Pro Xaa Leu Glu Pro
1 5

<210> SEQ ID NO 4
<211> LENGTH: 7
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Val can be optionally modified with a lower alkyl or alkanoyl
<221> NAME/KEY: MOD_RES
<222> LOCATION: (4)..(4)
<223> OTHER INFORMATION: Xaa can be Arg, Lys , Ser or Asn
<221> NAME/KEY: MOD_RES
<222> LOCATION: (7)..(7)
<223> OTHER INFORMATION: Pro is optionally amid ated

<400> SEQUENCE: 4

Val Asp Pro Xaa Leu Glu Pro
1 5

<210> SEQ ID NO 5
<211> LENGTH: 10
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Lys is optionally modi fied with a lower alkyl or alkanoyl
<221> NAME/KEY: MOD_RES
<222> LOCATION: (2)..(2)
<223> OTHER INFORMATION: Xaa can be Gly or Ala
<221> NAME/KEY: MOD_RES
<222> LOCATION: (10)..(10)
<223> OTHER INFORMATION: Lys is optionally amid ated

<400> SEQUENCE: 5

Lys Xaa Leu Gly Ile Ser Tyr Gly Arg Lys
1 5 10

<210> SEQ ID NO 6
<211> LENGTH: 7
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Arg is optionally modi fied with a lower alkyl or alkanoyl
<221> NAME/KEY: MOD_RES
<222> LOCATION: (3)..(3)
<223> OTHER INFORMATION: Xaa can be Ala, Pro , Ser or Gln
<221> NAME/KEY: MOD_RES
<222> LOCATION: (4)..(4)
<223> OTHER INFORMATION: Xaa can be Pro or His
<221> NAME/KEY: MOD_RES
<222> LOCATION: (5)..(5)
<223> OTHER INFORMATION: Xaa can be Gln or Pro
<221> NAME/KEY: MOD_RES -continued
<222> LOCATION: (6)..(6)
<223> OTHER INFORMATION: Xaa can be Asp, Asn , Gly or Ser
<221> NAME/KEY: MOD_RES
<222> LOCATION: (7)..(7)
<223> OTHER INFORMATION: Ser can be optionally amidated

<400> SEQUENCE: 6

Arg Arg Xaa Xaa Xaa Xaa Ser
1 5

<210> SEQ ID NO 7
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Ser is optionally modi fied with a lower alkyl or alkanoyl
<221> NAME/KEY: MOD_RES
<222> LOCATION: (3)..(3)
<223> OTHER INFORMATION: Xaa can be Asn or Thr
<221> NAME/KEY: MOD_RES
<222> LOCATION: (6)..(6)
<223> OTHER INFORMATION: Xaa can be Ala or Val
<221> NAME/KEY: MOD_RES
<222> LOCATION: (12)..(12)
<223> OTHER INFORMATION: Pro is optionally amid ated

<400> SEQUENCE: 7

Ser Gln Xaa His Gln Xaa Ser Leu Ser Lys G ln Pro
1 5 10

<210> SEQ ID NO 8
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (3)..(3)
<223> OTHER INFORMATION: Xaa can be Arg, Lys , Ser or Asn
<221> NAME/KEY: MOD_RES
<222> LOCATION: (5)..(5)
<223> OTHER INFORMATION: Xaa can be Glu or Asp
<221> NAME/KEY: MOD_RES
<222> LOCATION: (8)..(8)
<223> OTHER INFORMATION: Xaa can be Lys or Asn and can be optionally amidated

<400> SEQUENCE: 8

Asp Pro Xaa Leu Xaa Pro Trp Xaa
1 5

<210> SEQ ID NO 9
<211> LENGTH: 8
<212> TYPE: PRT
<213> ORGANISM: Human immunodeficiency virus type 1
<220> FEATURE:
<221> NAME/KEY: MOD_RES
<222> LOCATION: (3)..(3)
<223> OTHER INFORMATION: Xaa can be Arg, Lys , Ser or Asn
<221> NAME/KEY: MOD_RES
<222> LOCATION: (5)..(5)
<223> OTHER INFORMATION: Xaa can be Glu or Asp
<221> NAME/KEY: MOD_RES
<222> LOCATION: (8)..(8)
<223> OTHER INFORMATION: Xaa can be Lys or Asn

<400> SEQUENCE: 9

-continued

Asp Pro Xaa Leu Xaa Pro Trp Xaa
1 5

<210> SEQ ID NO 10
<211> LENGTH: 10
<212> TYPE: PRT
<213> ORGANISM: Human immunodeficiency virus type 1
<220> FEATURE:
<221> NAME/KEY: MOD_RES
<222> LOCATION: (2)..(2)
<223> OTHER INFORMATION: Xaa can be Gly or Ala

<400> SEQUENCE: 10

Lys Xaa Leu Gly Ile Ser Tyr Gly Arg Lys
1 5 10

<210> SEQ ID NO 11
<211> LENGTH: 8
<212> TYPE: PRT
<213> ORGANISM: Human immunodeficiency virus type 1

<400> SEQUENCE: 11

Leu Gly Ile Ser Tyr Gly Arg Lys
1 5

<210> SEQ ID NO 12
<211> LENGTH: 260
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Glu is attached to DnaK (HSP70)

<400> SEQUENCE: 12

Glu Pro Val Asp Pro Arg Leu Glu Pro Trp L ys Gly Ser Glu Pro Val
1 5 10 15

Asp Pro Arg Leu Glu Pro Trp Lys Gly Ser G lu Pro Val Asp Pro Arg
20 25 30

Leu Glu Pro Trp Lys Gly Ser Glu Pro Val A sp Pro Arg Leu Glu Pro
35 40 45

Trp Lys Gly Ser Glu Pro Val Asp Pro Asn L eu Glu Pro Trp Lys Gly
50 55 60

Ser Glu Pro Val Asp Pro Asn Leu Glu Pro T rp Lys Gly Ser Glu Pro
65 70 75 80

Val Asp Pro Asn Leu Glu Pro Trp Lys Gly S er Glu Pro Val Asp Pro
85 90 95

Asn Leu Glu Pro Trp Lys Gly Ser Glu Pro V al Asp Pro Ser Leu Glu
100 105 110

Pro Trp Lys Gly Ser Glu Pro Val Asp Pro S er Leu Glu Pro Trp Lys
115 120 125

Gly Ser Glu Pro Val Asp Pro Ser Leu Glu P ro Trp Lys Gly Ser Glu
130 135 140

Pro Val Asp Pro Ser Leu Glu Pro Trp Lys G ly Ser Glu Pro Val Asp
145 150 155 160

Pro Lys Leu Glu Pro Trp Lys Gly Ser Glu P ro Val Asp Pro Lys Leu
165 170 175

Glu Pro Trp Lys Gly Ser Glu Pro Val Asp P ro Lys Leu Glu Pro Trp
180 185 190

Lys Gly Ser Glu Pro Val Asp Pro Lys Leu G lu Pro Trp Lys Gly Ser

-continued 195 200 205

Lys Gly Leu Gly Ile Ser Tyr Gly Arg Lys S er Gly Ser Lys Gly Leu
210 215 220

Gly Ile Ser Tyr Gly Arg Lys Ser Gly Ser L ys Gly Leu Gly Ile Ser
225 230 235 240

Tyr Gly Arg Lys Ser Gly Ser Lys Gly Leu G ly Ile Ser Tyr Gly Arg
245 250 255

Lys Ser Gly Ser
260

<210> SEQ ID NO 13
<211> LENGTH: 380
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Glu is attached to DnaK (HSP70)

<400> SEQUENCE: 13

Glu Pro Val Asp Pro Arg Leu Glu Pro Trp L ys Gly Ser Glu Pro Val
1 5 10 15

Asp Pro Arg Leu Glu Pro Trp Lys Gly Ser G lu Pro Val Asp Pro Arg
20 25 30

Leu Glu Pro Trp Lys Gly Ser Glu Pro Val A sp Pro Arg Leu Glu Pro
35 40 45

Trp Lys Gly Ser Glu Pro Val Asp Pro Asn L eu Glu Pro Trp Lys Gly
50 55 60

Ser Glu Pro Val Asp Pro Asn Leu Glu Pro T rp Lys Gly Ser Glu Pro
65 70 75 80

Val Asp Pro Asn Leu Glu Pro Trp Lys Gly S er Glu Pro Val Asp Pro
85 90 95

Asn Leu Glu Pro Trp Lys Pro Trp Lys Gly S er Glu Pro Val Asp Pro
100 105 110

Ser Leu Glu Pro Trp Lys Gly Ser Glu Pro V al Asp Pro Lys Leu Glu
115 120 125

Pro Trp Lys Gly Ser Glu Pro Val Asp Pro L ys Leu Glu Pro Trp Lys
130 135 140

Gly Ser Glu Pro Val Asp Pro Lys Leu Glu P ro Trp Lys Gly Ser Glu
145 150 155 160

Pro Val Asp Pro Lys Leu Glu Pro Trp Lys G ly Ser Glu Pro Val Asp
165 170 175

Pro Asn Leu Ala Pro Trp Asn Gly Ser Glu P ro Val Asp Pro Asn Leu
180 185 190

Ala Pro Trp Asn Gly Ser Glu Pro Val Asp P ro Asn Leu Ala Pro Trp
195 200 205

Asn Gly Ser Glu Pro Val Asp Pro Asn Leu A la Pro Trp Asn Gly Ser
210 215 220

Glu Pro Val Asp Pro Asn Leu Glu Pro Trp A sn Gly Ser Glu Pro Val
225 230 235 240

Asp Pro Asn Leu Glu Pro Trp Asn Gly Ser G lu Pro Val Asp Pro Asn
245 250 255

Leu Glu Pro Trp Asn Gly Ser Glu Pro Val A sp Pro Asn Leu Glu Pro
260 265 270

Trp Asn Gly Ser Glu Pro Val Asp Pro Ser L eu Glu Pro Trp Asn Gly
275 280 285

-continued

```
Ser Glu Pro Val Asp Pro Ser Leu Glu Pro T rp Asn Gly Ser Glu Pro
    290                 295                 300

Val Asp Pro Ser Leu Glu Pro Trp Asn Gly S er Glu Pro Val Asp Pro
305                 310                 315                 320

Ser Leu Glu Pro Trp Asn Gly Ser Glu Pro V al Asp Pro Lys Leu Glu
                325                 330                 335

Pro Trp Asn Gly Ser Glu Pro Val Asp Pro L ys Leu Glu Pro Trp Asn
            340                 345                 350

Gly Ser Glu Pro Val Asp Pro Lys Leu Glu P ro Trp Asn Gly Ser Glu
        355                 360                 365

Pro Val Asp Pro Lys Leu Glu Pro Trp Asn G ly Ser
    370                 375                 380
```

<210> SEQ ID NO 14
<211> LENGTH: 13
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Cys is conjugated with  Diphtheria toxoid
<221> NAME/KEY: MOD_RES
<222> LOCATION: (13)..(13)
<223> OTHER INFORMATION: Lys is attached to an amide.

<400> SEQUENCE: 14

```
Cys Gly Ser Lys Gly Leu Gly Ile Ser Tyr G ly Arg Lys
1               5                   10
```

<210> SEQ ID NO 15
<211> LENGTH: 72
<212> TYPE: PRT
<213> ORGANISM: Human immunodeficiency virus type 1

<400> SEQUENCE: 15

```
Met Glu Pro Val Asp Pro Arg Leu Glu Pro T rp Lys His Pro Gly Ser
1               5                   10                  15

Gln Pro Lys Thr Ala Cys Thr Asn Cys Tyr C ys Lys Lys Cys Cys Phe
            20                  25                  30

His Cys Gln Val Cys Phe Ile Thr Lys Gly L eu Gly Ile Ser Tyr Gly
        35                  40                  45

Arg Lys Lys Arg Arg Gln Arg Arg Arg Ala P ro Gln Asp Ser Gln Thr
    50                  55                  60

His Gln Val Ser Leu Ser Lys Gln
65                  70
```

<210> SEQ ID NO 16
<211> LENGTH: 12
<212> TYPE: PRT
<213> ORGANISM: Human immunodeficiency virus type 1
<220> FEATURE:
<221> NAME/KEY: MOD_RES
<222> LOCATION: (3)..(3)
<223> OTHER INFORMATION: Xaa can be Arg, Lys , Ser or Asn
<221> NAME/KEY: MOD_RES
<222> LOCATION: (5)..(5)
<223> OTHER INFORMATION: Xaa can be Glu or Asp
<221> NAME/KEY: MOD_RES
<222> LOCATION: (8)..(8)
<223> OTHER INFORMATION: Xaa can be Lys or Asn
<221> NAME/KEY: MOD_RES
<222> LOCATION: (12)..(12)
<223> OTHER INFORMATION: Ser is attached to an amide -continued

<400> SEQUENCE: 16

Asp Pro Xaa Leu Xaa Pro Trp Xaa His Pro G ly Ser
1 5 10

<210> SEQ ID NO 17
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Lys is optionally amid ated

<400> SEQUENCE: 17

Asp Pro Arg Leu Glu Pro Trp Lys
1 5

<210> SEQ ID NO 18
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Asn is optionally amid ated

<400> SEQUENCE: 18

Asp Pro Asn Leu Glu Pro Trp Asn
1 5

<210> SEQ ID NO 19
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Lys is optionally amid ated

<400> SEQUENCE: 19

Asp Pro Lys Leu Glu Pro Trp Lys
1 5

<210> SEQ ID NO 20
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Lys is optionally amid ated

<400> SEQUENCE: 20

Asp Pro Ser Leu Glu Pro Trp Lys

-continued 1 5

<210> SEQ ID NO 21
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Lys is optionally amid ated

<400> SEQUENCE: 21

Asp Pro Asn Leu Glu Pro Trp Lys
1 5

<210> SEQ ID NO 22
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Asn is optionally amid ated

<400> SEQUENCE: 22

Asp Pro Lys Leu Glu Pro Trp Asn
1 5

<210> SEQ ID NO 23
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Asn is optionally amid ated

<400> SEQUENCE: 23

Asp Pro Asn Leu Asp Pro Trp Asn
1 5

<210> SEQ ID NO 24
<211> LENGTH: 8
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Asp is optionally modi fied with a lower alkyl or alkanoyl
<221> NAME/KEY: MOD_RES
<222> LOCATION: (8)..(8)
<223> OTHER INFORMATION: Asn is optionally amid ated

<400> SEQUENCE: 24

Asp Pro Ser Leu Glu Pro Trp Asn
1 5

-continued

<210> SEQ ID NO 25
<211> LENGTH: 14
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Lys can be optionally modified with a lower alkyl or alkanoyl
<221> NAME/KEY: MOD_RES
<222> LOCATION: (2)..(2)
<223> OTHER INFORMATION: Xaa can be Gly or Ala

<400> SEQUENCE: 25

Lys Xaa Leu Gly Ile Ser Tyr Gly Arg Lys G ly Ser Gly Ser
1 5 10

<210> SEQ ID NO 26
<211> LENGTH: 8
<212> TYPE: PRT
<213> ORGANISM: Human immunodeficiency virus type 1
<220> FEATURE:
<221> NAME/KEY: MOD_RES
<222> LOCATION: (5)..(5)
<223> OTHER INFORMATION: Xaa can be Glu or Asp

<400> SEQUENCE: 26

Asp Pro Asn Leu Xaa Pro Trp Asn
1 5

<210> SEQ ID NO 27
<211> LENGTH: 4
<212> TYPE: PRT
<213> ORGANISM: Human immunodeficiency virus type 1

<400> SEQUENCE: 27

Ser Gly Ser Gly
1

<210> SEQ ID NO 28
<211> LENGTH: 9
<212> TYPE: PRT
<213> ORGANISM: Human immunodeficiency virus type 1

<400> SEQUENCE: 28

Val Asp Pro Arg Leu Glu Pro Trp Asn
1 5

<210> SEQ ID NO 29
<211> LENGTH: 9
<212> TYPE: PRT
<213> ORGANISM: Human immunodeficiency virus type 1

<400> SEQUENCE: 29

Val Asp Pro Asn Leu Asp Pro Trp Asn
1 5

<210> SEQ ID NO 30
<211> LENGTH: 9
<212> TYPE: PRT
<213> ORGANISM: Human immunodeficiency virus type 1

<400> SEQUENCE: 30

Val Asp Pro Ser Leu Asp Pro Trp Asn
1 5

<210> SEQ ID NO 31

-continued

<211> LENGTH: 9
<212> TYPE: PRT
<213> ORGANISM: Human immunodeficiency virus type 1

<400> SEQUENCE: 31

Val Asp Pro Asn Leu Asp Pro Trp Lys
1               5

<210> SEQ ID NO 32
<211> LENGTH: 11
<212> TYPE: PRT
<213> ORGANISM: Human immunodeficiency virus type 1

<400> SEQUENCE: 32

Glu Pro Val Asp Pro Asn Leu Asp Pro Trp L ys
1               5                   10

<210> SEQ ID NO 33
<211> LENGTH: 10
<212> TYPE: PRT
<213> ORGANISM: Human immunodeficiency virus type 1

<400> SEQUENCE: 33

Lys Ala Leu Gly Ile Ser Tyr Gly Arg Lys
1               5                   10

<210> SEQ ID NO 34
<211> LENGTH: 13
<212> TYPE: PRT
<213> ORGANISM: Human immunodeficiency virus type 1
<220> FEATURE:
<221> NAME/KEY: MOD_RES
<222> LOCATION: (13)..(13)
<223> OTHER INFORMATION: C terminal Lys is a midated

<400> SEQUENCE: 34

Cys Gly Ser Lys Gly Leu Gly Ile Ser Tyr G ly Arg Lys
1               5                   10

<210> SEQ ID NO 35
<211> LENGTH: 12
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: biotin is attached to N-terminal Ser

<400> SEQUENCE: 35

Ser Gly Ser Gly Leu Gly Ile Ser Tyr Gly A rg Lys
1               5                   10

<210> SEQ ID NO 36
<211> LENGTH: 4
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Biotin is attached to Ser

<400> SEQUENCE: 36

Ser Gly Ser Gly
1

<210> SEQ ID NO 37
<211> LENGTH: 9

-continued

```
<212> TYPE: PRT
<213> ORGANISM: Human immunodeficiency virus type 1
<220> FEATURE:
<221> NAME/KEY: MOD_RES
<222> LOCATION: (4)..(4)
<223> OTHER INFORMATION: Xaa can be Arg, Lys , Ser or Asn
<221> NAME/KEY: MOD_RES
<222> LOCATION: (6)..(6)
<223> OTHER INFORMATION: Xaa can be Glu or Asp
<221> NAME/KEY: MOD_RES
<222> LOCATION: (9)..(9)
<223> OTHER INFORMATION: Xaa can be Lys or Asn and can be optionally
      amidated

<400> SEQUENCE: 37

Val Asp Pro Xaa Leu Xaa Pro Trp Xaa
1               5


<210> SEQ ID NO 38
<211> LENGTH: 11
<212> TYPE: PRT
<213> ORGANISM: Human immunodeficiency virus type 1
<220> FEATURE:
<221> NAME/KEY: MOD_RES
<222> LOCATION: (1)..(1)
<223> OTHER INFORMATION: Xaa can be Glu or Asp
<221> NAME/KEY: MOD_RES
<222> LOCATION: (6)..(6)
<223> OTHER INFORMATION: Xaa can be Arg, Lys , Ser or Asn
<221> NAME/KEY: MOD_RES
<222> LOCATION: (8)..(8)
<223> OTHER INFORMATION: Xaa can be Glu or Asp
<221> NAME/KEY: MOD_RES
<222> LOCATION: (11)..(11)
<223> OTHER INFORMATION: Xaa can be Lys or Asn and can be optionally
      amidated

<400> SEQUENCE: 38

Xaa Pro Val Asp Pro Xaa Leu Xaa Pro Trp X aa
1               5                   10


<210> SEQ ID NO 39
<211> LENGTH: 4
<212> TYPE: PRT
<213> ORGANISM: Human immunodeficiency virus type 1

<400> SEQUENCE: 39

Gly Ser Gly Ser
1
```

METHODS AND COMPOSITIONS FOR IMPAIRING MULTIPLICATION OF HIV-1

FIELD OF THE INVENTION

The present invention relates generally to compositions and methods useful for inhibiting the multiplication of human immunodeficiency virus-1 (HIV-1) in infected patients, symptomatic or asymptomatic, and for attenuating HIV-1 multiplication following primary infection in previously uninfected subjects, thus minimizing progression to AIDS.

BACKGROUND OF THE INVENTION

A variety of approaches to the treatment of human immunodeficiency virus type 1 (HIV-1) have focused on the transactivating (tαt) gene of HIV-1, which produces a protein (Tat) essential for transcription of the virus. The tαt gene and its protein have been sequenced and examined for involvement in proposed treatments of HIV [see, e.g., U.S. Pat. Nos. 5,158,877; 5,238,882; and 5,110,802; International Patent Application Nos. WO92/07871, WO91/10453, WO91/09958, and WO87/02989, published May 14, 1992, Jul. 25, 1991, Jul. 11, 1991 and May 21, 1987, respectively]. Tat protein is released extracellularly, making it available to be taken up by other infected cells to enhance transcription of HIV-1 in the cells and by noninfected cells, to alter host cell gene activations. Tat renders the cells susceptible to infection by the virus. Uptake of Tat by cells is very strong, and has been reported as mediated by a short basic sequence of the protein [S. Fawell et al., *Proc. Natl. Acad. Sci., USA*, 91:664–668 (1994)].

Immunization with HIV-1 Tat protein as a potential AIDS vaccine is under active investigation. The HXB/LAV HIV-1 Tat sequence has been used as the immunogen in reported studies, either as a recombinant protein [A. Cafaro et al, *Nat. Med.* 5:643–650 (1999)], a DNA vaccine [S. Calarota et al, *Lancet*, 351:1320–5 (1998)], inactivated protein (Tat toxoid) [S. S. Cohen et al, *Proc. Natl. Acad. Sci. USA*, 96(19):10842–10847 (1999); A. Gringeri et al, *J. Hum. Virol.*, 1:293–8 (1998)] or a DNA vaccine expressing inactive Tat [E. Caselli et al, *J. Immunol.*, 162:5631–5638 (1999)]. Immunizations with the full Tat sequence induced both cellular and humoral immunity. See, also, M. C. Rhe et al, *J. Acquir. Immmune Defic. Syndr. Hum. Virol.* 10:408–416 (1995), C. J. Li et al, *Proc. Natl. Acad, Sci. USA*, 94:8116–8120 (1997); and others].

International Patent Application No. WO92/14755, published Sep. 3, 1992, relates to the Tat protein and to the integrin cell surface receptor capable of binding to the Tat protein. Two Tat sequences that bind integrin are identified: -Arg-Lys-Lys-Arg-Arg-Gln-Arg-Arg-Arg- [SEQ ID NO: 1], as well as -Gly-Arg-Gly-Asp-Ser-Pro- [SEQ ID NO: 2]. These sequences are the basic region or domain which is the dominant binding site for the integrin. This specification demonstrates that a number of peptides corresponding to these Tat sequences and the corresponding integrins block in vitro cell binding to Tat coated plates, as do antibodies to the appropriate integrins. However, the specification also shows that these reagents do not block uptake of functional Tat by cells (see Example 9 in WO92/14755), thus nullifying the proposed mechanism of action for therapeutic benefit in HIV infection. The Tat sequences described in this international application are distinct from the peptide immunogens of the present invention.

Both monoclonal and polyclonal antibodies to Tat protein have been readily produced in animals and shown to block uptake of Tat protein in vitro [see, e.g., D. Brake et al, *J. Virol.*, 64:962 (1990); D. Mann et al, *EMBO J.*, 10: 1733 (1991); J. Abraham et al, cited above; P. Auron et al, cited above; M. Jaye et al, cited above; G. Zauli et al, cited above]. More recent reports showed that monoclonal or polyclonal antibodies to Tat protein added to tissue culture medium attenuated HIV-1 infection in vitro [L. Steinaa et al, *Arch. Virol.*, 139:263 (1994); M. Re et al, cited above; and G. Zauli et al, *J. Acq. Imm. Def. Syndr. Hum. Retrovirol.*, 10:306 (1995)].

The inventor's own publications [G. Goldstein, *Nature Med.*, 2:960 (1996), and International Patent Application No. WO95/3 1999, published Nov. 30, 1995] reviewed the evidence indicating that secretion of HIV-1 Tat protein from infected cells and uptake by both infected and uninfected cells was important for the infectivity of HIV-1. Previous studies also showed that antibodies to Tat protein in vitro blocked uptake of Tat and inhibited in vitro infectivity. Active immunization of mammals was suggested to induce antibodies to HIV-1 Tat protein as a potential AIDS vaccine. See, also, G. Goldstein et al, "Minimization of chronic plasma viremia in rhesus macaques immunized with synthetic HIV-1 Tat peptides and infected with a chimeric simian/human immunodeficiency virus ($SHIV_{33}$)", *Vaccine*, 18:2789 (2000).

Other publications by the inventor, International Patent Application No. WO99/02185, published Jan. 21, 1999, and U.S. Pat. No. 5,891,994, issued Apr. 6, 1999 (both incorporated by reference herein), revealed a new concept in treatment and prevention of HIV-1 infection that utilized Tat sequences which were recognized as epitopes by the rabbit immune system. Unlike the prior disclosures discussed above, these publications relate to therapeutic and immunogenic combinations requiring at least two, and preferably all four, of the Tat peptides or polypeptides comprising the "Epitope I" sequences spanning Tat amino acid residues 4 (or 5) through 10, as follows: -Asp-Pro-$X_7$-Leu-Glu-Pro- [SEQ ID NO: 3] or $R^1$-Val-Asp-Pro-$X_7$-Leu-Glu-Pro-$R^2$ [SEQ ID NO: 4], wherein $X_7$ is Arg, Lys, Ser or Asn. Such compositions induce antibodies that react with most HIV-1 Tat proteins and impair the multiplication of HIV-1. According to this publication, certain other Tat sequences, which comprise an "Epitope II" peptide or polypeptide spanning Tat amino acid residues 41–50 of the formula R3-Lys-$X_{42}$-Leu-Gly-Ile-Ser-Tyr-Gly-Arg-Lys-R4 [SEQ ID NO:5], wherein $X_{42}$ is selected from the group consisting of Gly or Ala, may be added to this composition. Alternatively, an "Epitope III" peptide or polypeptide spanning Tat amino acid residues 56–62 of the formula R5-Arg-Arg-$X_{58}$-$Z_{59}$-$A_{60}$-$Y_{61}$-Ser-R6 [SEQ ID NO:6], wherein $X_{58}$ is selected from the group consisting of Ala, Pro Ser and Gln; wherein $Y_{61}$ is selected from the group consisting of Asp, Asn, Gly and Ser; wherein $Z_{59}$ is selected from the group consisting of Pro and His; wherein $A_{60}$ is selected from the group consisting of Gln and Pro, may be added to this composition. Still alternatively, an "Epitope IV" peptide or polypeptide spanning Tat AA residues 62–73 of the formula R7-Ser-Gln-$X_{64}$-His-Gln-$Y_{67}$-Ser-Leu-Ser-Lys-Gln-Pro-R8 [SEQ ID NO:7], wherein $X_{64}$ is selected from the group consisting of Asn and Thr; wherein $Y_{67}$ is selected from the group consisting of Ala and Val, may be added to this composition. The composition itself may be employed to induce antibodies to a large number of Tat sequences characteristic of the multiple variants of HIV-1. The compositions or antibodies generated are used as vaccine or prophylactic treatments against these multiple variants.

Despite the growing knowledge about HIV-1 disease progression, there remains a need in the art for the development of compositions and methods for treatment of HIV-1, both prophylactically and therapeutically, which are useful to lower the viral levels of HIV-1 for the treatment and possible prevention of the subsequent, generally fatal, AIDS disease.

SUMMARY OF THE INVENTION

In one aspect, the present invention provides a composition comprising at least two variants of a peptide or polypeptide of the Epitope I formula R1-Asp-Pro-$Y_7$-Leu-$X_9$-Pro-Trp-$Z_{12}$-R2 [SEQ ID NO:8], wherein $Y_7$ is selected from the group consisting of Arg, Lys, Ser and Asn; wherein $X_9$ is selected from the group consisting of Glu and Asp; wherein $Z_{12}$ is selected from the group consisting of Lys and Asn; wherein R1 is selected from the group consisting of hydrogen, a lower alkyl, a lower alkanoyl, and a sequence of between 1 to about 5 amino acids, optionally substituted with a lower alkyl or lower alkanoyl; wherein R2 is selected from the group consisting of a free hydroxyl, an amide, and a sequence of one or up to about 5 additional amino acids, optionally substituted with an amide. In this composition, at least one of the two variants must have the formula wherein $Y_7$ is Arg and $Z_{12}$ is Lys, and at least a second of the two variants must have the formula in which $Y_7$ is Asn and $Z_{12}$ is Asn. Each peptide of this composition is recognized as an HIV-1 Tat Epitope I by a primate immune system. This formula permits the construction and use of a variety of peptide combinations.

In another aspect, the above-described composition further contains one or more additional peptide or polypeptide (s) which represent other amino acid sequences which correspond to HIV-1 Tat amino acid residues 5 through amino acid residue 12. These optional amino acid sequences are described in detail below. These sequences are preferably from an HIV-1 strain with a Tat protein variant at that location.

In another aspect, this invention provides a composition described above that contains peptides or polypeptides which comprise at least the two required Epitope I peptides, recognized by primates (and preferably additional Epitope I peptides), in combination with one or more HIV-1 Tat Epitopes II, III and/or IV. Epitopes II, III and IV are the HIV-1 Tat peptide formulae described in International Patent Publication No. WO99/02185, incorporated herein by reference. Such compositions can combine appropriate HIV-1 Tat peptides, so as to provide for a composition that induces antibodies reactive with greater than about 95% of all known HIV-1 Tat proteins.

In yet a further aspect, the invention provides an antibody composition comprising at least one antibody, preferably generated in a primate, which specifically binds to a peptide or polypeptide of the formula R1-Asp-Pro-$Y_7$-Leu-$X_9$-Pro-Trp-$Z_{12}$-R2 [SEQ ID NO:8], wherein $Y_7$ is selected from the group consisting of Arg, Lys, Ser and Asn; wherein $X_9$ is selected from the group consisting of Glu and Asp; wherein $Z_{12}$ is selected from the group consisting of Lys and Asn; wherein R1 is selected from the group consisting of hydrogen, a lower alkyl, a lower alkanoyl, and a sequence of between 1 to about 5 amino acids, optionally substituted with a lower alkyl or lower alkanoyl; wherein R2 is selected from the group consisting of a free hydroxyl, an amide, and a sequence of one or up to about 5 additional amino acids, optionally substituted with an amide. This antibody composition preferably comprises at least two antibodies, i.e., one antibody which binds to the Epitope I variant in which $Y_7$ is Arg and $Z_{12}$ is Lys, and at least a second antibody which binds to a second Epitope I variant in which $Y_7$ is Asn and $Z_{12}$ is Asn. Other antibodies directed to other variants than the two specified variants may also be included in this composition. These antibodies in the composition bind to Epitope I sequences recognized by the primate immune system, which epitope is present on multiple variants of HIV-1 Tat proteins. These antibodies include a variety of antibody constructs, such as monoclonal antibodies, as described in detail below.

In still another aspect, the invention provides an antibody, particularly a monoclonal antibody, which specifically binds to a primate-recognized epitope of an HIV Tat protein, the epitope comprising the amino acid sequence -Asp-Pro-$Y_7$-Leu-$X_9$-Pro-Trp-$Z_{12}$- [SEQ ID NO:9], wherein $Y_7$, $X_9$ and $Z_{12}$ are defined as above.

In yet another aspect, the invention provides an antibody composition comprising at least one antibody that recognizes Epitope II peptide sequence -Lys-$X_{42}$-Leu-Gly-Ile-Ser-Tyr-Gly-Arg-Lys- [SEQ ID NO: 10], where $X_{42}$ is Gly or Ala, as a distinct epitope from previously described antibodies which recognize the epitope of -Leu-Gly-Ile-Ser-Tyr-Gly-Arg-Lys-[SEQ ID NO: 11]. Preferably, the composition comprises one antibody which recognizes both the peptide in which $X_{42}$ is Gly and the peptide in which $X_{42}$ is Ala. These antibodies are preferably generated in primates. These antibodies in the composition bind to Epitope II sequences recognized by the primate immune system, which epitope is present on multiple variants of HIV-1 Tat proteins. These antibodies include a variety of antibody constructs, as described in detail below.

In still another aspect, the invention provides an antibody, preferably a monoclonal antibody, that recognizes Epitope II peptide sequence -Lys-$X_{42}$-Leu-Gly-Ile-Ser-Tyr-Gly-Arg-Lys- [SEQ ID NO: 10], where $X_{42}$ is Gly or Ala, as a distinct epitope from the epitope of -Leu-Gly-Ile-Ser-Tyr-Gly-Arg-Lys- [SEQ ID NO: 11], recognized by previously described antibodies.

In yet a further aspect, the invention provides a recombinant or synthetic gene which encodes sequentially a peptide or polypeptide that contains at least two variants of a peptide or polypeptide of the Epitope I formula R1-Asp-Pro-$Y_7$-Leu-$X_9$-Pro-Trp-$Z_{12}$-R2 [SEQ ID NO: 8], as defined above. In this synthetic gene, at least one of the two variants must have the formula wherein $Y_7$ is Arg and $Z_{12}$ is Lys, and at least a second of the two variants must have the formula in which $Y_7$ is Asn and $Z_{12}$ is Asn. Optionally, this synthetic gene comprises a carboxy terminal Epitope II peptide, as recognized by the primate immune system. Alternatively, the recombinant or synthetic gene contains the seven or eight preferred primate-recognized Epitope I amino acid sequences identified below. The synthetic gene may contain each amino acid sequence separated by a spacer sequence, or may express each peptide/polypeptide in an open reading frame with a carrier protein. The synthetic gene may be separated from the carrier protein by a spacer if the spacer is fused to a primate-recognized Epitope I sequence, leaving an Epitope II sequence at the carboxy terminus of the recombinant protein. Further embodiments include multiple Epitope I peptides of the above formula fused together and to the carrier protein.

In yet a further aspect, the invention provides a synthetic molecule, e.g., a vector, comprising the above-described synthetic gene, operatively linked to regulatory nucleic acid sequences which direct and control expression of the product of the synthetic gene in a host cell.

In another aspect, the invention provides a recombinant microorganism, e.g., a virus or commensal bacterium, which contains the above described synthetic gene or synthetic molecule. This microorganism is capable of expressing multiple copies of the product of the gene or molecule in a host.

Still another aspect of the invention is a pharmaceutical composition useful for inducing antibodies that react with a large number of known HIV-1 Tat proteins, e.g., greater than 95%, and preferably greater than 99%, of the known Tat proteins. These induced antibodies can impair the multiplication of HIV-1. The pharmaceutical composition comprises at least one of the recombinant or synthetic peptide/polypeptide compositions described above, or the synthetic gene/molecule described above; or the recombinant microorganism described above, in a pharmaceutically acceptable carrier.

Still a further aspect of the invention is a pharmaceutical composition useful for impairing the multiplication of HIV-1, this composition containing an above described antibody composition or monoclonal antibody composition.

In yet a further aspect of the invention, a method for reducing the viral levels of HIV-1 involves exposing a human or other primate to antibody-inducing pharmaceutical compositions described above, actively inducing antibodies that react with most HIV-1 Tat proteins, and impairing the multiplication of the virus in vivo. This method is appropriate for an HIV-1 infected subject with a competent immune system, or an uninfected or chronically infected, but asymptomatic, subject. The method induces antibodies which react with HIV-1 Tat proteins, and which reduce viral multiplication during any initial acute infection with HIV-1 and which further minimize chronic viremia which leads to AIDS.

In still another aspect, the invention provides a method for reducing the viral levels of HIV-1 by administering to a human, who is incapable of mounting an effective or rapid immune response to infection with HIV-1, a pharmaceutical composition containing the antibody compositions described above. The method can involve chronically administering the composition.

Yet other aspects of the invention include methods for producing the compositions described above, as well as host cells transfected with such compositions.

Still another aspect of this invention is a kit useful for the measurement and detection of titers and specificities of antibodies induced by immunization with the compositions described above. The kit of the invention includes preferably the two required Epitope I peptides described above, as well as addition peptides of the Epitope I, recognized by primates, and possibly additional peptides of Epitopes II through IV, and coated solid supports, a labeled reagent for detecting the binding of antibodies to these peptides, and miscellaneous substrates and apparatus for evoking or detecting the signals provided by the labels, as well as conventional apparatus for taking blood samples, appropriate vials and other diagnostic assay components.

In yet a further aspect, the invention provides a method for detecting the titers and reactivity patterns of antibodies in subjects immunized with the compositions of this invention. The method includes the steps of incubating dilutions of the subject's biological fluid, e.g. serum, with plates or beads on which are bound one or more peptides of the Epitope I sequences of this invention and optionally, the Epitopes II through IV, washing away unbound biological materials, and measuring any antibody binding to the peptides with labeled reagent, e.g., an anti-human immunoglobulin to which is associated an enzyme. Depending on the type of label employed, the signal produced by the label may be evoked by further adding a substrate which reacts with the enzyme, e.g., producing a color change. Other conventional labels may also be incorporated into this assay design.

Other aspects and advantages of the present invention are described further in the following detailed description of the preferred embodiments thereof.

BRIEF DESCRIPTION OF THE DRAWINGS

FIG. 3A illustrates the design of a pentavalent Epitope I/Epitope II HIV-1 Tat immunogenic construct in three letter amino acid code [SEQ ID NO: 12].

FIG. 3B illustrates the design of an octavalent universal Epitope I in three letter amino acid code [SEQ ID NO: 13].

FIG. 3C illustrates the design of an univalent universal Epitope II immunogenic construct in three letter amino acid code [SEQ ID NO: 14].

DETAILED DESCRIPTION OF THE INVENTION

Figure 1A:
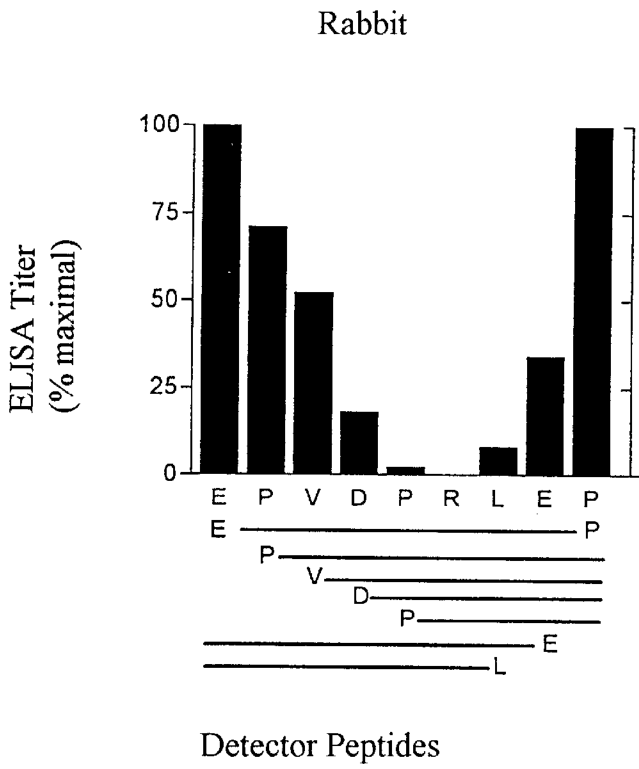
FIG. 1A is a graph of ELISA titers of rabbit antiserum to larger linear Epitope I peptides on truncated detector peptides, expressed as a percentage of maximal binding to larger peptides. The N- or C-terminal amino acids of the corresponding detector peptides are shown below each column in single letter code.

The present invention provides a solution to the above-stated problem by providing additional compositions which induce antibodies in uninfected or early stage HIV-1 infected subjects still capable of mounting an immune response to an immunogen, the antibodies reacting with a large number (i.e., greater than 95%, and preferably, greater than 99%) of known HIV-1 Tat protein variants. The term "Tat sequence (or protein) variant" means a polypeptide or peptide containing Tat protein amino acid residues, or a sequence from another HIV-1 strain Tat protein that is substantially similar to the consensus sequence of Table I [SEQ ID NO: 15]. Each variant may differ from the consensus sequence and/or from another variant by at least one amino acid change within the residues of interest for Epitopes I through IV. This change may provide the same or different antigenic specificity to that particular Tat Epitope when added to the composition of the invention.

The antibodies induced by compositions of this invention can inhibit multiplication of HIV-1, which prevents further disease progression to AIDS. Antibody compositions are also provided for use in infected or non-infected humans, who are incapable of mounting an effective or rapid immune response to HIV-1 infection. These compositions are capable of reacting with large numbers of Tat proteins, thus reducing viral levels of HIV-1. These antibodies are useful in both therapeutic and prophylactic contexts to control the development of AIDS in a large population exposed to, or infected by, HIV-1 strains which produce upon infection immunologically distinct Tat proteins.

The compositions of the present invention include peptides or proteins, based on peptides provided by an epitope of HIV-1 Tat protein to which primates developed antibodies, or nucleic acid sequences which encode the peptides and polypeptides that induce antibodies to Tat in primates. These induced antibodies, in turn, impair multiplication of HIV-1.

HIV-1 Tat protein is produced from two exons: Exon 1 encodes a 72 amino acid (AA) protein which may be expressed without splicing or which may be spliced with the approximately 15–32 amino acids encoded by Exon 2. The HIV-1 Tat Exon I sequence appears in Table I, and is a consensus sequence based on Tat protein sequences of 31 known HIV-1 strains found in the common B subtype [NIH Los Alamos database]. The amino acid positions in which variations appear are in lower case letters. In Table I [SEQ ID NO: 15], the amino acid residue at position 73 is the first Pro of Exon 2 of HIV-1 Tat. Since the 72 amino acid product of Exon 1 is capable alone of cellular uptake and activation, it is essential that antibodies react with and interdict intercellular transport of the 72 amino acid peptide. HIV-1 Tat contains a cysteine-rich region between AA positions 22 and 37 of Exon 1 [SEQ ID NO: 15], with a single covalent bond between $Cys_{21}$ and $Cys_{37}$, producing a complex tertiary structure. The scientific literature has indicated that this region does not appear to be immunogenic. Predominant antibodies to Tat are to the linear N-terminal Pro-rich region (AA1–21) and to the linear basic region (AA44–65), with an additional antibody reported to AA62–73.

The inventor has previously identified epitopes, i.e., binding regions, recognized by rabbit antibodies (antigenic sequences) in the N-terminal linear sequence 1–21 (22 AA) of Exon 1 [SEQ ID NO: 15] of Tat variants, and had defined four B cell epitopes in HIV-1 Tat. As previously described in International Patent Publication WO99/02185, immunogenic regions of this larger sequence were recognized by the rabbit immune system. These regions are identified in the consensus sequence of Exon 1 in Table I below: Epitope I was identified by rabbit antibodies as the nine amino acid sequence of AA positions 2–10 of Exon 1. Epitope II was identified as the eight amino acid sequence of AA positions 43–50 of Exon 1. Epitope III was identified as the 7 amino acid sequence of AA positions 56–62 of Exon 1. Epitope IV was identified as the twelve amino acid sequence of AA positions 62–73 of Tat, including the first Pro (AA 73) of Exon 2, and overlaps Ser 62 of Epitope III.

TABLE I

| Consensus Tat Sequence |
|---|
| 1 10 20 |
| Met glu Pro Val asp pro arg Leu Glu Pro Trp lys His Pro Gly Ser Gln Pro Iys thr |
| 30 40 |
| ala cys thr asn Cys Tyr Cys Lys lys Cys Cys phe his Cys gln val Cys Phe ile thr |
| 50 60 |
| Lys gly Leu gly Ile Ser Tyr Gly Arg Lys Lys Arg Arg Gln Arg arg arg ala pro gln |
| 70 |
| asp Ser gln thr his Gln val ser Leu ser Lys gln [SEQ ID NO: 15] |

In the present invention, however, the inventor has detected a surprising shift in the amino acid sequences of particularly Epitope I recognized by B cells in primates. In Table I, Epitope I and II sequences recognized by primates are underlined. Primate-recognized Epitope I spans Tat amino acid residues 5 to 12. The sequence of Epitope II recognized by B cells in primates spans amino acids 41–50. Epitopes III and IV are the same epitopes recognized in rabbits, as reported in WO99/02 185, incorporated herein by reference.

A. Primate Recognized-Epitope I Immunogenic Compositions

In one embodiment, the present invention provides a composition containing at least two variants of a peptide or polypeptide recognized by the primate immune system, and eliciting a specific humoral immune response (for the purpose of this invention) in a primate exposed to the sequences in vivo. These primate-recognized Epitope I amino acid sequences correspond to amino acid residues 5–12 of the Tat consensus sequence [SEQ ID NO:15] of Table I, derived from a number of "Tat sequence variants". Primate-recognized Epitope I defines peptides of the general formula: R1-Asp-Pro-$Y_7$-Leu-$X_9$-Pro-Trp-$Z_{12}$-R2 [SEQ ID NO: 8], wherein $Y_7$ is Arg, Lys, Ser or Asn; $X_9$ is Glu or Asp; and $Z_{12}$ is Lys or Asn. This formula permits a variety of variant mammalian Epitope I peptides. The composition of this invention must contain at least one peptide variant wherein $Y_7$ is Arg and $Z_{12}$ is Lys, and at least a second peptide variant in which $Y_7$ is Asn and $Z_{12}$ is Asn.

The specified amino acids appearing in the formula of primate-recognized Epitope I above is a minimum reactive primate Epitope I sequence. Each immunogen defined by that formula which is employed in methods of this invention to raise antibodies to the minimum Epitope I sequence may be a larger amino acid sequence. For example, the minimum Epitope I amino acids are flanked by other amino acids, so that the entire Epitope I immunogenic sequence is between 8 and about 25 amino acids in length. The identity of the flanking amino acids is not essential to the biological function of the Epitope I immunogen. In particular, additional amino acids on the N-terminus of primate-recognized Epitope I sequences do not affect immunogenicity. Thus, for each primate-recognized Epitope I peptide, the N-terminal R1 may be a free hydrogen on the unmodified N terminal amino acid, or a lower alkyl (i.e., C1–C10 alkyl), or a lower C1–C10 alkanoyl, such as an acetyl group. R1 may also include a sequence of between 1 to about 5 amino acids, optionally substituted with a lower alkyl or lower alkanoyl. Preferably, R1 represents 2 amino acids. In one embodiment, RI is Val. In another embodiment, R1 is -$X_2$-Pro-Val-, wherein $X_2$ is Glu or Asp. Preferably, R1 represents 3 amino acids.

Additional amino acids on the C-terminus of the primate-recognized Epitope I minimum sequence can enhance antibody titer. While the C-terminal R2 can be a simple free hydroxyl group on the C terminal amino acid, it can also be a C terminal amide. However, to enhance titer, R2 is preferably a sequence of between 1 to about 14, preferably about 4 additional amino acids amidated at the carboxyl terminus. In a preferred embodiment, R2 is -His-Pro-Gly-Ser-amide [SEQ ID NO:16].

Preferably a composition of this invention includes in addition to the two required peptides identified above, at least five or six different amino acid sequences of the primate-recognized Epitope I formula. Most preferably, the composition comprises seven or eight variant amino acid sequences, identified immediately below. The composition may also contain other peptide or polypeptide sequences, each containing a different $X_9$, $Y_7$ and $Z_{12}$ combination. As demonstrated in the examples below, with three sites of antigenic variability in the primate-recognized Epitope I, a preferred composition of this invention may contain sufficient peptides of primate-recognized Epitope I to comprise 95% of all known B clade and non-B clade HIV-I Tat variants by including the two "required" peptides:

R1-Asp-Pro-Arg-Leu-Glu-Pro-Trp-Lys-R2 [SEQ ID NO:17]; and

R1-Asp-Pro-Asn-Leu-Glu-Pro-Trp-Asn-R2 [SEQ ID NO:18], as well as one to five of the following additional Epitope I peptides:

R1-Asp-Pro-Lys-Leu-Glu-Pro-Trp-Lys-R2 [SEQ ID NO:19];

R1-Asp-Pro-Ser-Leu-Glu-Pro-Trp-Lys-R2 [SEQ ID NO:20];

R1-Asp-Pro-Asn-Leu-Glu-Pro-Trp-Lys-R2 [SEQ ID NO:21];

R1-Asp-Pro-Lys-Leu-Glu-Pro-Trp-Asn-R2 [SEQ ID NO:22]; and

R1-Asp-Pro-Asn-Leu-Asp-Pro-Trp-Asn-R2 [SEQ ID NO:23]; as well as still optionally, the rare variant R1-Asp-Pro-Ser-Leu-Glu-Pro-Trp-Asn-R2 [SEQ ID NO: 24].

The primate-recognized Epitope I composition of the invention may contain a number of additional peptides or polypeptides that contain other sequences which correspond to amino acid residues between AA 5 to AA 12 of SEQ ID NO:15, but are derived from other Tat variants which do not cross-react well with antibodies to the primate-recognized Epitope I compositions. The Epitope I compositions of this invention may contain multiple copies of five or more different Epitope I peptides, in any order. In one embodiment, at least one copy of seven or all eight of the amino acid sequences described above [SEQ ID NOs: 17–24] are present.

These peptides or polypeptides of the invention are produced synthetically or recombinantly. Optional amino acids (e.g., -Gly-Ser-) or other amino acid or chemical compound spacers may be included at the termini of the peptides for the purpose of linking the peptides together or to a carrier. This composition may take the form of one or more of the above-described peptides expressed as a synthetic peptide coupled to a carrier protein. Alternatively, a composition may contain multiple Epitope I peptides, each expressed as a multiple antigenic peptide, optionally coupled to carrier protein. Alternatively, the selected peptides may be linked sequentially and expressed within a recombinantly produced protein. As one embodiment, the eight specifically identified sequences above are linked sequentially, with and without spacer amino acids therebetween, to form a larger recombinant protein. Alternatively, the recombinant protein may be fused in frame with a carrier protein. These primate Epitope I compositions are designed to induce antibodies reactive with greater than 95% of the known variants of the HIV-1 Tat protein including Tat proteins of the HIV-1 B and non-B clades.

Primate-recognized Epitope I compositions demonstrate a biological activity of inducing in an immunized, immune competent primate, i.e., a non-infected human, or an asymptomatic infected human, an active humoral immune response (i.e., antibodies) that is directed against greater than 95%, and preferably greater than 99%, of the known variants of Tat proteins of HIV-1. The end result of such treatment is an impairment of the multiplication of HIV-1 following an acute infection. This impairment prevents high post-seroconversion plasma levels of HIV-1 associated with progression to AIDS. Active induction of antibodies in the asymptomatic phase of HIV infection may reduce viral multiplication, lower the plasma viral load and reduce the likelihood of progression to AIDS. The composition which contains at least the two required primate-recognized Epitope I immunogens, and preferably seven or eight of those Epitope I sequences [e.g., SEQ ID NO: 17–24], can elicit an immune response to about 95% of 294 known Tat sequences of the common B subtypes of HIV-1 and with Tat proteins of all 56 non-B HIV-1 subtypes that have been sequenced [courtesy of Dr. Esther Guzman, Los Alamos NIAID HIV database; GenBank database].

B. Immunogenic Compositions Containing Additional Epitopes

In another embodiment, the present invention provides other compositions which employ two or more primate-recognized Epitope I sequences combined with at least one Epitope II sequence and, optionally with one or more Epitope III or IV peptides. These HIV-1 Tat Epitopes II, III and IV, as recognized by the rabbit immune system, are described in detail in International Patent Application No. WO99/02185, incorporated herein by reference.

Briefly described, the Epitope II sequence elicits a specific humoral immune response in a primate exposed to the Epitope II sequence in vivo. Epitope II, as recognized by primates, defines peptides of the formula R3-Lys-$X_{42}$-Leu-Gly-Ile-Ser-Tyr-Gly-Arg-Lys-R4 [SEQ ID NO: 5], wherein $X_{42}$ is Gly or Ala. The minimum epitope recognized by the primate immune system is that of the specifically-identified amino acids of that formula, i.e., -Lys-Gly-Leu-Gly-Ile-Ser-Tyr-Gly Arg-Lys- (amino acids 41–50 of SEQ ID NO: 15). This is also the sequence of the presently preferred immunogen for Epitope II. This immunogen in which $X_{42}$ is Gly induces antibodies cross-reactive with the sequence in which $X_{42}$ is Ala. This would react/cross-react with greater than 95% of known HIV-1 Tat proteins. This Epitope II sequence has no antigenic variability in a large number of known HIV-1 Tat variants. The N terminal R3 may represent the hydrogen on the unmodified N terminal amino acid Lys, or R3 may be a lower alkyl, or a lower alkanoyl, such as an acetyl group, substituent on the Lys. R3 may also include a sequence of between 1 to about 5 amino acids, optionally substituted with a lower alkyl or lower alkanoyl. The C terminal R4 may represent the free hydroxyl of the C terminal amino acid, or R4 may be an amide on that C terminal amino acid. R4 may include additional non-polar amino acids, such as a spacer of sequence -Gly-Ser-Gly-Ser- [SEQ ID NO: 25] or some other amino acid sequence. However, R4 cannot be the basic amino acids -Lys-Arg-Arg- which naturally occur in the Tat sequence after the last amino acid in the Epitope II formula. This Epitope II sequence found in 294 B clade Tat variants is recognized by primates (As reported in WO99/02185, the rabbit immune system recognizes the epitope from AA43–50 of SEQ ID NO: 15).

Epitope II is poorly immunogenic when presented within other sequences. Thus, for optimal immunogenicity, this sequence is prepared as a synthetic peptide fused to, or coupled to, a carrier protein or as a multiple antigenic peptide, optionally coupled to carrier protein. Alternatively, Epitope II may be expressed as the C terminal sequence of a recombinant protein, which is optionally fused in frame to a carrier protein at its amino terminal sequence. In a composition of this invention, an Epitope II peptide is preferably presented alone or in combination with one or more primate-recognized Epitope I peptides.

Briefly described and as identified in WO99/02185, Epitope III defines peptides of the formula: R5-Arg-Arg-$X_{58}$-$Z_{59}$-$A_{60}$-$Y_{61}$-Ser-R6 [SEQ ID NO: 6], wherein $X_{58}$ may be Ala, Pro, Ser or Gln; $Y_{61}$ may be Asp, Asn, Gly or Ser; $Z_{59}$ may be Pro or His; and $A_{60}$ may be Gln or Pro. Epitope IV defines peptides of the formula: R7-Ser-Gln-$X_{64}$-His-Gln-$Y_{67}$-Ser-Leu-Ser-Lys-Gln-Pro-R8 [SEQ ID NO: 7], wherein $X_{64}$ may be Asn or Thr; and $Y_{67}$ may be Ala or Val.

Thus, the compositions of this invention, i.e., the peptide/polypeptides containing the above-identified amino acid sequences, when provided to a human subject, are useful in the immunologic interdiction of extracellular Tat proteins of most HIV-1 strains. These compositions function to critically reduce chronic multiplication of the virus and permit effective immune control of the virus.

The immunogens for each Epitope are preferably designed to induce antibodies reactive with the highest proportion of naturally occurring variants of each epitope. For an epitope such as primate-recognized Epitope I, multiple copies of an immunogen could be incorporated in a synthetic or recombinant immunogen to enhance the immunogenicity and produce higher titer antibodies. Furthermore, immunogens for two or more epitopes could be combined to extend coverage, since variations in sequence of each epitope occur independently. Thus, as one example, a composition of this invention contains the two required primate-recognized Epitope I peptides, as well as four or five of the other Epitope I peptides specifically identified above with a Cys on the terminus, which is coupled to carrier protein. Alternatively, multiple antigenic peptides may be prepared, optionally coupled to carrier protein, and combined to form a composition of this invention. Alternatively, mixtures of two or more immunogens could be used.

The primate-recognized Epitope I immunogens of this invention, with or without any Epitope II, III or IV or other optional immunogens, may be prepared and used in immunogenic compositions in a variety of forms, for example, chemically synthesized or as recombinant peptides, polypeptides, proteins, fusion proteins or fused peptides.

1. Recombinant or Synthetic Peptide/Proteins Coupled to a Carrier

As one embodiment, a composition of the present invention may be a synthetic or recombinantly-produced peptide, containing at least the two required primate-recognized Epitope I immunogenic amino acid sequences (as well as additional other Epitope I sequences) and also containing one or more Epitope II/III/IV immunogenic amino acid sequences, coupled to a selected carrier protein. In this embodiment of a composition of this invention, multiple above-described primate-recognized Epitope I amino acid sequences with or without flanking sequences, may be combined sequentially in a polypeptide and coupled to the same carrier. Alternatively, the Epitope I, II, III, or IV immunogens, may be coupled individually as peptides to the same or a different carrier proteins, and the resulting immunogen-carrier constructs mixed together to form a single composition. Such sequences may be made synthetically by conventional methods of chemical synthesis or recombinantly by expression in a selected host cell, also by now-conventional means.

For this embodiment, the carrier protein is desirably a protein or other molecule which can enhance the immunogenicity of the selected immunogen. Such a carrier may be a larger molecule which has an adjuvanting effect. Exemplary conventional protein carriers include, without limitation, *E. coli* DnaK protein, galactokinase (galK, which catalyzes the first step of galactose metabolism in bacteria), ubiquitin, α-mating factor, β-galactosidase, and influenza NS-1protein. Toxoids (i.e., the sequence which encodes the naturally occurring toxin, with sufficient modifications to eliminate its toxic activity) such as diphtheria toxoid and tetanus toxoid may also be employed as carriers. Similarly a variety of bacterial heat shock proteins, e.g., mycobacterial hsp-70 may be used. Glutathione reductase (GST) is another useful carrier. One of skill in the art can readily select an appropriate carrier.

In a particularly desirable immunogen-carrier protein construct, the two required Epitope I immunogens and three to six additional primate-recognized Epitope I immunogens and optional immunogenic peptides/polypeptides may be covalently linked to a mycobacterial *E. coli* heat shock protein 70 (hsp70) [K. Suzue et al, *J. Immunol.*, 156:873 (1996)]. In another desirable embodiment, the composition is formed by covalently linking the immunogen-containing peptide or polypeptide sequences to diphtheria toxoid.

2. Multiple Antigenic Peptide

In yet another embodiment, the peptides or polypeptide epitope immunogens and any selected optional immunogens may be in the form of a multiple antigenic peptide ("MAP", also referred to as an octameric lysine core peptide) construct. Such a construct may be designed employing the MAP system described by Tam, *Proc. Natl. Acad. Sci. USA*, 85:5409–5413 (1988). This system makes use of a core matrix of lysine residues onto which multiple copies of the same primate-recognized Epitope I of the invention are synthesized as described [D. Posnett et al., *J. Biol. Chem.*, 263(4):1719–1725 (1988); J. Tam, "Chemically Defined Synthetic Immunogens and Vaccines by the Multiple Antigen Peptide Approach", *Vaccine Research and Developments*, Vol. 1, ed. W. Koff and H. Six, pp. 51–87 (Marcel Deblau, Inc., New York 1992)]. Each MAP contains multiple copies of only one peptide. Therefore, a composition containing MAPs will contain at least two, and preferably about seven, MAPs. One MAP will have the first required peptide or polypeptide Epitope I immunogen attached to each lysine core; a second MAP will have the second required peptide or polypeptide Epitope I immunogen attached to each lysine core. Still other MAPs, each with a different primate-recognized Epitope I amino acid sequence identified above, may be included. Multiple different MAPs may be employed to obtain any desired combination of Epitope II, III or IV sequences. Preferably these MAP constructs are associated with other T cell stimulatory sequences, or as pharmaceutical compositions, administered in conjunction with T cell stimulatory agents, such as known adjuvants.

3. Spacers

In either of the above compositions, e.g., as peptide/polypeptide-carrier constructs or MAPs, each peptide/polypeptide immunogen, or each amino acid sequence in the immunogen, may be optionally separated by an optional amino acid sequence called a "spacer". Spacers are sequences of between 1 to about 4 amino acids which are interposed between two sequences to permit linkage therebetween without adversely affecting the three dimensional structure of the immunogen. Spacers may also contain restriction endonuclease cleavage sites to enable separation of the sequences, where desired. Suitable spacers or linkers are known and may be readily designed and selected by one of skill in the art. Preferred spacers are sequences containing Gly and/or Ser amino acids.

F. Nucleic Acid Compositions of the Invention, Including a Synthetic or Recombinantly-Produced Gene Other embodiments of this invention include nucleic acid sequences that encode the above-described primate-recognized Epitope I peptide/polypeptide compositions, including the peptide and polypeptide immunogens of the compositions described above, and including those peptides and polypeptides fused to carrier proteins. The nucleic acid sequences may also include sequences encoding the carrier proteins.

Thus, one preferred embodiment of the invention is a "synthetic gene" that encodes sequentially for at least the two required primate-recognized Epitope I immunogenic peptides/polypeptides. Note that while the gene is referred to as "synthetic", it may be designed by chemical synthesis or recombinant means, as desired. The synthetic gene preferably encodes seven or all eight of the specifically identified primate-recognized Epitope I amino acid sequences [SEQ ID NOS: 17–24]. The synthetic gene can also encode any selection of an Epitope II or III immunogen, provided that the Epitope II or III peptide is fused to the C terminus of the primate-recognized Epitope I sequence and not further modified on its own C terminus. The synthetic gene may encode multiple copies of the two required Epitope I amino acid sequences, or copies of additional multiple different immunogens or amino acid sequences, or multiple copies of multiple different immunogens or amino acid sequences. The synthetic gene may encode the selected amino acid sequences in an open reading frame with, or fused to, a nucleic acid sequence encoding a carrier protein. A further characteristic of the synthetic gene may be that it encodes a spacer between each sequence encoding an immunogen and/or between the sequence encoding an immunogen and the sequence encoding the carrier protein.

The synthetic gene of the present invention may also be part of a synthetic or recombinant molecule. The synthetic molecule may be a nucleic acid construct, such as a vector or plasmid which contains the synthetic gene encoding the protein, peptide, polypeptide, fusion protein or fusion peptide under the operative control of nucleic acid sequences encoding regulatory elements such as promoters, termination signals, and the like. Such synthetic molecules may be used to produce the polypeptide/peptide immunogen compositions recombinantly. The synthetic gene or synthetic molecule can be prepared by the use of chemical synthetic methods or preferably, by recombinant techniques. For example, the synthetic gene or molecule may contain certain preference codons for the species of the indicated host cell.

The synthetic gene or molecule, preferably in the form of DNA, may be used in a variety of ways. For example, these synthetic nucleic acid sequences may be employed to express the peptide/polypeptides of the invention in vitro in a host cell culture. The expressed immunogens, after suitable purification, may then be incorporated into a pharmaceutical reagent or vaccine. Alternatively, the synthetic gene or synthetic molecule of this invention may be administered directly into a mammal, preferably a human, as so-called 'naked DNA' to express the protein/peptide immunogen in vivo in a patient. See, e.g., J. Cohen, *Science*, 259:1691–1692 (Mar. 19, 1993); E. Fynan et al., *Proc. Natl. Acad. Sci., USA*, 90:11478–11482 (December 1993); and J. A. Wolff et al., *Biotechniques*, 11:474–485 (1991), all incorporated by reference herein. The synthetic molecule, e.g., a vector or plasmid, may be used for direct injection into the mammalian host. This results in expression of the protein by host cells and subsequent presentation to the immune system to induce antibody formation in vivo.

G. Microorganisms That Express The Synthetic Gene

In still another aspect of the present invention, the synthetic genes or molecules of this invention may be incorporated into a non-pathogenic microorganism. The resulting microorganism, when administered to a mammalian host, expresses and multiplies the expressed compositions of this invention in vivo to induce specific antibody formation. For example, non-pathogenic recombinant viruses or commensal bacterium which carry the compositions or synthetic genes of this invention and are useful for administration to a mammalian patient may be prepared by use of conventional methodology and selected from among known non-pathogenic microorganisms.

Among commensal bacterium which may be useful for exogenous delivery of the synthetic molecule to the patient, and/or for carrying the synthetic gene into the patient in vivo, include, without limitation, various strains of *Streptococcus*, e.g., *S. gordonii*, or *E. coli, Bacillus, Streptomyces*, and *Saccharomyces.*

Suitable non-pathogenic viruses which may be engineered to carry the synthetic gene into the cells of the host include poxviruses, such as vaccinia, adenovirus, adeno-associated viruses, canarypox viruses, retroviruses and the like. A number of such non-pathogenic viruses are commonly used for human gene therapy, and as carriers for other vaccine agents, and are known and selectable by one of skill in the art.

H. Preparation or Manufacture of Compositions of the Invention

The compositions of the invention, and the individual polypeptides/peptides containing the primate-recognized Epitope I immunogens of this invention and optionally one or more Epitope II, III or IV, the synthetic genes, and synthetic molecules of the invention, may be prepared conventionally by resort to known chemical synthesis techniques, such as described by Merrifield, *J. Amer. Chem. Soc.*, 85:2149–2154 (1963). Alternatively, the compositions of this invention may be prepared by known recombinant DNA techniques by cloning and expressing within a host microorganism or cell a DNA fragment carrying a sequence encoding a peptide/polypeptide containing at least the two required primate-recognized Epitope I sequences with optional other immunogens and optional carrier proteins. Coding sequences for the Epitope I and optional immunogens can be prepared synthetically [W. P. C. Stemmer et al, *Gene*, 164:49 (1995)] or can be derived from viral RNA by known techniques, or from available cDNA-containing plasmids.

Combinations of these techniques may be used. For example, assembly of sequential immunogens by conventional molecular biology techniques may be used for production of the synthetic gene, and site-directed mutagenesis used to provide desired sequences of immunogens. The product of the synthetic gene is then produced recombinantly. All of these manipulations may be performed by conventional methodology.

Systems for cloning and expressing the peptide/polypeptide compositions of this invention using the synthetic genes or molecules include the use of various microorganisms and cells which are well known in recombinant technology. These include, for example, various strains of *E. coli, Bacillus, Streptomyces*, and *Saccharomyces*, as well as mammalian, yeast and insect cells. Suitable vectors therefor are known and available from private and public laboratories and depositories and from commercial vendors. Currently, the most preferred hosts are mammalian cells, such as Chinese Hamster ovary cells (CHO) or COS-1 cells. These hosts may be used in connection with poxvirus vectors, such as vaccinia or swinepox. The selection of other suitable host cells and methods for transformation, culture, amplification, screening and product production and purification can be performed by one of skill in the art by reference to known techniques. See, e.g., Gething and Sambrook, *Nature*, 293:620–625 (1981),. among others. Another preferred system includes the baculovirus expression system and vectors.

When produced by conventional recombinant means, the compositions of this invention, i.e., the polypeptide/peptides containing the indicated copies of the primate-recognized Epitope I immunogens and optional immunogens may be isolated either from the cellular contents by conventional lysis techniques or from cell medium by conventional methods, such as chromatography. See, e.g., Sambrook et al., *Molecular Cloning. A Laboratory Manual.*, 2d Edit., Cold Spring Harbor Laboratory, New York (1989). Suitable plasmid and viral vectors used either for production of the peptide/polypeptide components as DNA vaccines are well known to those of skill in the art and are not a limitation of the present invention. See, Sambrook et al., cited above and the references above to production of the protein. See, also International Patent Application PCT WO94/01139, published Jan. 20, 1994. Briefly, the DNA encoding the selected peptide/polypeptide is inserted into a vector or plasmid which contains other optional flanking sequences, a promoter, an mRNA leader sequence, an initiation site and other regulatory sequences capable of directing the multiplication and expression of that sequence in vivo or in vitro. These vectors permit infection of the patient's cells and expression of the synthetic gene sequence in vivo or expression of it as a protein/peptide or fusion protein/peptide in vitro.

The resulting composition may be formulated into a primate-recognized Epitope I composition with any number of optional immunogens and screened for efficacy by in vivo assays. Such assays employ immunization of an animal, e.g., a simian, with the composition, and evaluation of titers of antibody to the Tat proteins of HIV-1 or to synthetic detector peptides corresponding to variant Tat sequences (as shown in the examples below).

I. Antibody Compositions of the Invention

An antibody composition or ligand-binding composition of this invention encompasses at least one antibody which specifically binds to an Epitope I of the formula -Asp-Pro-$Y_7$-Leu-$X_9$-Pro-Trp-$Z_{12}$- [SEQ ID NO: 9], wherein $Y_7$ is selected from the group consisting of Arg, Lys, Ser and Asn; wherein $X_9$ is selected from the group consisting of Glu and Asp; and wherein $Z_{12}$ is selected from the group consisting of Lys and Asn. Preferably, such an antibody composition includes at least two or more different antibodies or ligands which specifically bind to at least the two required Epitope I sequences, as defined herein. Antibodies (or other binding ligands) are generated to the two required sequences R1-Asp-Pro-Arg-Leu-Glu-Pro-Trp-Lys-R2 [SEQ ID NO: 17]; and R1-Asp-Pro-Asn-Leu-Glu-Pro-Trp-Asn-R2 [SEQ ID NO: 18] of Epitope I. The antibodies of the composition thus bind an HIV Tat protein present on multiple variants of HIV-1 Tat proteins. Additional antibodies or ligands are generated to other sequences falling within the Epitope I formula above.

In one embodiment, an isolated antibody directed which binds the Epitope I peptide or polypeptide of the invention, as described above, is also an aspect of this invention. Such polyclonal antibody compositions are typically produced by immunizing a mammal, preferably a primate, with a peptide/polypeptide composition containing the two required Epitope I immunogens, as well as an assortment of other primate-recognized Epitope I immunogens and optional immunogens, as described above. Particularly desirable as immunogens are a heptavalent primate-recognized Epitope I immunogen (i.e., without the rare variant) or an octavalent immunogen, such as the synthetic gene or fusion protein described in Example 3 below, and/or a univalent Epitope II immunogen (i.e., a single Epitope II peptide, optionally bound to a carrier). In additional to being generated in primates, such antibodies may also be produced in transgenic animals, including so-called "humanized" transgenic mice. However, a desirable host for raising polyclonal antibodies to a composition of this invention includes humans. The titer of such polyclonal antibodies raised in the mammal exposed to the Epitope I compositions can be monitored by standard techniques, such as with an enzyme-linked immunosorbent assay. If desired, the antibody molecules can be isolated from the mammal, e.g., from the whole blood, plasma or serum, and further purified from the plasma or serum of the immunized mammal by conventional techniques. Conventional harvesting techniques can include plasmapheresis, protein A chromatography, among others. Such polyclonal antibody compositions may themselves be employed as pharmaceutical compositions of this invention.

Alternatively, antibody producing cells may be obtained from the mammals and used to prepare other forms of antibodies and ligands, e.g., monoclonal antibodies, chimeric antibodies, humanized antibodies, human antibodies, ligands produced by screening phage displays, antibody fragments and mixtures thereof, and synthetic antibodies, monoclonal antibodies, chimeric antibodies, humanized antibodies and fully human antibodies. Preparative techniques for generation of these types of ligands are known and the ligands themselves may be generated using the disclosed amino acid sequences of the primate-recognized Epitope I and optional immunogens. See, e.g., Kohler and Milstein (1975) *Nature*, 256:495–497; Kozbor et al, (1983) *Immunol. Today*, 4:72; Cole et al, 1985, Monoclonal Antibodies and Cancer Therapy, Alan R. Liss, Inc., pp. 77–96; Harlow et al., *Antibodies A Laboratory Manual*, Cold Spring Harbor Laboratory, (1988); Queen et al., *Proc. Nat'l. Acad. Sci. USA*, 86:10029–10032 (1989); Hodgson et al., *Bio/Technology*. 9:421 (1991); International PCT Application PCT/GB91/01554, Publication No. WO92/04381 and International PCT Application PCT/GB93/00725, Publication No. WO93/20210].

For example, in another embodiment, a monoclonal antibody specifically binds to the minimum Epitope I sequence defined by -Asp-Pro-$Y_7$-Leu-$X_9$-Pro-Trp-$Z_{12}$- [SEQ ID NO: 9] of an HIV Tat protein: comprising any larger immunogen defined by the Epitope I formula, with the variable amino acids and R groups as defined above. As one embodiment, a monoclonal antibody binds specifically to the amino acid sequence -Asp-Pro-Asn-Leu-$X_9$-Pro-Trp-Asn- [SEQ ID NO:26], wherein $X_9$ is Glu or Asp. Still other monoclonal antibodies which bind specifically to the minimum Epitope I sequences defined by the formula above are part of this invention.

In another embodiment of this invention, a monoclonal antibody specifically binds to a minimum Epitope II sequence comprising the amino acid sequence -Lys-$X_{42}$-Leu-Gly-Ile-Ser-Tyr-Gly-Arg-Lys- [SEQ ID NO: 10], where $X_{42}$ is Gly or Ala, as a distinct epitope from the epitope of-Leu-Gly-Ile-Ser-Tyr-Gly-Arg-Lys- [SEQ ID NO: 11], recognized by previously described antibodies. Preferably, an antibody composition comprises one antibody which is cross-reactive with both the peptide in which $X_{42}$ is Gly and the peptide in which $X_{42}$ is Ala. These antibodies are preferably generated in primates. Still other monoclonal antibodies which bind specifically to the minimum Epitope II sequences defined by the formula above are part of this invention.

Other anti-Tat antibodies may be developed by screening a recombinant combinatorial immunoglobulin library (e.g., antibody phage displays) with primate-recognized HIV-1 Tat epitopes of this invention to isolate immunoglobulin library members that bind to the HIV-1 Tat [W. D. Huse et al., *Science*, 246:1275–1281 (1988)]. Kits for generating and screening phage display libraries are commercially available, e.g., Pharmacia Recombinant Phage Antibody System, Catalog No. 27-9400-01, Strategene Phage Display kits, etc. See, e.g., U.S. Pat. No. , 5,223,409, International Publication No. WO92/09690, WO90/02809, etc. Chimeric antibodies may similarly be developed using known techniques [Morrison et al, (1984) *Proc. Natl. Acad., Sci., USA*, 81:6851; Takeda et al, *Nature*, 313:452(1984), among others]. Chimeric antibodies are molecules in which different portions are derived from different animal species. Single chain antibodies may also be prepared by conventional methods [see, e.g., U.S. Pat. Nos. 4,946,778 and 4,704,692] using the variable portions of the polyclonal or monoclonal antibodies produced according to this invention. Antibody fragments, such as the Fab, $F(ab')_2$ and Fv fragments and libraries thereof may also be employed in various aspects of this invention.

These antibody/ligand compositions desirably bind to most known HIV-1 Tat protein variants (e.g., greater than 95%, and preferably greater than 99% of known Tat protein variants), and prevent the Tat proteins from supporting further HIV-1 multiplication. Such compositions can include a mixture of multiple different antibodies which bind HIV-1 Tat protein epitope sequences from multiple strains of HIV-1. Thus, these antibodies are useful in pharmaceutical methods and formulations described below.

J. Pharmaceutical Compositions of the Invention

As another aspect of this invention, a pharmaceutical composition useful for inducing antibodies that react with most (e.g., greater than 95%, preferably greater than 99%) known HIV-1 Tat proteins and impair the multiplication of HIV-1 can comprise as its active agents, at least the two required primate-recognized Epitope I peptides or polypeptides of this invention, and preferably additional Epitope I peptides. Several desirable compositions include the following above-described components:

(a) a peptide/polypeptide immunogen which contains at least the two required, and more preferably at least seven, of the primate-recognized Epitope I amino acid sequences [SEQ ID NOS:17–24];

(b) a peptide/polypeptide immunogen of (a) which further contains any of the Epitope II, III or IV amino acid sequences, preferably a univalent Epitope II immunogen;

(c) a synthetic or recombinantly-produced gene encoding the two required primate-recognized Epitope I sequences and preferably seven of the Epitope I sequences [SEQ ID NO: 17–24], and optional sequences as described above;

(f) a synthetic molecule containing the synthetic gene of (c);

(g) a recombinant virus carrying the synthetic gene or molecule described above; and (h) a commensal bacterial carrying the synthetic gene or molecule described above.

The selected active component(s) is present in a pharmaceutically acceptable carrier, and the composition may contain additional ingredients. Pharmaceutical formulations containing the compositions of this invention may contain other active agents, such as T cell stimulatory agents for the MAPs, adjuvants and immunostimulatory cytokines, such as IL-12, and other well-known cytokines, for the protein/peptide compositions. All of these pharmaceutical compositions can operate to lower the viral levels of a mammal.

As pharmaceutical compositions, the compositions comprising primate-recognized Epitope I peptide or nucleic acid sequences and the optional immunogen sequences are admixed with a pharmaceutically acceptable vehicle suitable for administration to mammals for prophylaxis or treatment of virus infections. The proteins/peptides may be combined in a single pharmaceutical preparation for administration. Suitable pharmaceutically acceptable carriers for use in an immunogenic proteinaceous composition of the invention are well known to those of skill in the art. Such carriers include, for example, saline, buffered saline, a selected adjuvant, such as aqueous suspensions of aluminum and magnesium hydroxides, liposomes, oil in water emulsions and others. Suitable adjuvants may also be employed in the protein-containing compositions of this invention. Suitable vehicles for direct DNA, plasmid nucleic acid, or recombinant vector administration include, without limitation, saline, or sucrose, protamine, polybrene, polylysine, polycations, proteins, $CaPO_4$ or spermidine. See e.g, PCT application WO94/01139 and the references cited above. The peptide/polypeptide compositions and synthetic genes or molecules in vivo are capable of eliciting in an immunized host mammal, e.g., a human, an immune response capable of interdicting multiple (e.g., greater than about 95 to about 99%) known extracellular Tat protein variants from HIV-1 and thereby lowering the viral levels.

Yet another pharmaceutical composition useful for impairing the multiplication of HIV-1 comprises an antibody composition containing one or more of the antibodies described in detail above. In a pharmaceutical composition, the antibodies may be carried in a saline solution or other suitable carrier. The antibody compositions are capable of providing an immediate, exogenously provided, interdiction of Tat.

The present invention is not limited by the selection of the conventional, physiologically acceptable, carriers, adjuvants, or other ingredients useful in pharmaceutical preparations of the types described above. The preparation of these pharmaceutically acceptable compositions, from the above-described components, having appropriate pH isotonicity, stability and other conventional characteristics is within the skill of the art.

K. Method of the Invention—Impairing Multiplication of HIV-1

According to the present invention, a method for reducing the viral levels of HIV-1 involves exposing a human to the Tat antibody-inducing pharmaceutical compositions described above, actively inducing antibodies that react with multiple (e.g., greater than 95%, preferably greater than 99% of the known) HIV-1 Tat proteins, and impairing the multiplication of the virus in vivo. This method is appropriate for an HIV-1 infected subject with a competent immune system, or for active immunization of an uninfected subject. The method induces antibodies which react with HIV-1 Tat proteins, reduce viral multiplication during an initial acute infection with HIV-1 and minimize chronic viremia leading to AIDS. This method also lowers chronic viral multiplication in infected subjects, again minimizing progression to AIDS. Use of these methods can control chronic HIV-1 infection, providing a novel mechanism of treatment not subject to the development of resistance. The antibodies to Tat inhibit replication of HIV-1 quasispecies independently of the Tat that they are producing, since the extracellular Tat protein is not associated with the replicating moiety of the virus. Hence, there is no obvious mechanism by which Tat antibodies could generate selective pressure for non-reactive, escape Tat variants.

According to this method, the pharmaceutical compositions preferably contain the peptide/polypeptide compositions, the synthetic genes or molecules, the recombinant virus or the commensal recombinant bacterium. Preferably the compositions contain a heptavalent synthetic gene or fusion protein (without the rare variant of Epitope I) or the octavalent synthetic gene or fusion protein of Example 3 and optionally a univalent Epitope II peptide. Each of these active components of the pharmaceutical composition actively induces in the exposed human the formation of anti-Tat antibodies which block the transfer of Tat from infected cells to other infected or uninfected cells. This action reduces the multiplicity of infection and blocks the burst of HIV-1 viral expansion, and thus lowers viral levels. In already infected patients, this method of reduction of viral levels can reduce chronic viremia and progression to AIDS. In uninfected humans, this administration of the compositions of the invention can reduce acute infection and thus minimize chronic viremia leading to progression to AIDS.

Yet another aspect of the invention is a method for reducing the viral levels of HIV-1 by administering to a human incapable of mounting an effective or rapid immune response to infection with HIV-1, a pharmaceutical composition containing the antibody compositions described above. The method can involve chronically administering the composition. Among such patients suitable for treatment with this method are HIV-1 infected patients who are immunocompromised by disease and unable to mount a strong immune response. In later stages of HIV infection, the likelihood of generating effective titers of antibodies is less, due to the immune impairment associated with the disease. Also among such patients are HIV-1 infected pregnant women, neonates of infected mothers, and unimmunized patients with putative exposure (e.g., a human who has been inadvertently "stuck" with a needle used by an HIV-1 infected human).

For such patients, the method of the invention preferably employs as the pharmaceutical composition an antibody composition of the invention. The antibody composition includes a polyclonal antibody composition prepared in other mammals, preferably normal humans or alternatively, the other forms of antibody described above, e.g., monoclonal, etc. These antibody compositions are administered as passive immunotherapy to inhibit viral multiplication and lower the viral load. The exogenous antibodies which react with multiple known Tat proteins from HIV-1 provide in the patient an immediate interdiction of the transfer of Tat from virally infected cells to other infected or uninfected cells. According to this method, the patient may be chronically treated with the antibody composition for a long treatment regimen.

In each of the above-described methods, the compositions of the present invention are administered by an appropriate route, e.g., by the subcutaneous, oral, intravenous, intraperitoneal, intramuscular, nasal, or inhalation routes. The presently preferred route of administration is intramuscular for the immunizing (active induction) compositions and intravenous (i.v.), subcutaneous (s.c.), or intramuscular (i.m.) for the antibody (passive therapy) compositions. A recombinant viral vector or naked DNA is preferably administered intramuscularly; however, other certain recombinant viral vectors and/or live commensal bacteria may be delivered orally.

The amount of the protein, peptide or nucleic acid sequences of the invention present in each vaccine dose is selected with regard to consideration of the patient's age, weight, sex, general physical condition and the like. The amount of active component required to induce an immune response, preferably a protective response, or produce an exogenous effect in the patient without significant adverse side effects varies depending upon the pharmaceutical composition employed and the optional presence of an adjuvant (for the protein-containing compositions).

Generally, for the compositions containing protein/peptide, fusion protein, MAP or coupled protein, or antibody composition, each dose will comprise between about 50 $\mu$g to about 20 mg of the peptide/polypeptide immunogens per mL of a sterile solution. A more preferred dosage may be about 500 $\mu$g of immunogen. Other dosage ranges may also be contemplated by one of skill in the art. Initial doses may be optionally followed by repeated boosts, where desirable.

The antibody compositions of the present invention can be employed in chronic treatments for subjects at risk of acute infection due to needle sticks or maternal infection. A dosage frequency for such "acute" infections may range from daily dosages to once or twice a week i.v., s.c., or i.m., for a duration of about 6 weeks. The antibody compositions of the present invention can also be employed in chronic treatments for infected patients, or patients with advanced HIV. In infected patients, the frequency of chronic administration may range from daily dosages to once or twice per month i.v., s.c., or i.m., and may depend upon the half-life of the immunogen (e.g., about 7–21 days). However, the duration of chronic treatment for such infected patients is anticipated to be an indefinite, but prolonged period.

Alternatively, compositions of this invention may be designed for direct administration of synthetic genes or molecules of this invention as "naked DNA". As with the protein immunogenic compositions, the amounts of components in the DNA and vector compositions and the mode of administration, e.g., injection or intranasal, may be selected and adjusted by one of skill in the art. Generally, each dose will comprise between about 50 $\mu$g to about 1 mg of immunogen-encoding DNA per mL of a sterile solution.

For recombinant viruses containing the synthetic genes or molecules, the doses may range from about 20 to about 50 ml of saline solution containing concentrations of from about $1\times10^7$ to $1\times10^{10}$ pfu/ml recombinant virus of the present invention. A preferred human dosage is about 20 ml saline solution at the above concentrations. However, it is understood that one of skill in the art may alter such dosages depending upon the identity of the recombinant virus and the make-up of the immunogen that it is delivering to the host.

The amounts of the commensal bacteria carrying the synthetic gene or molecules to be delivered to the patient will generally range between about $10^3$ to about $10^{12}$ cells/kg. These dosages may be altered by one of skill in the art depending upon the bacterium being used and the particular composition containing Epitope I and optional immunogens being delivered by the live bacterium.

Thus, the compositions of this invention are designed to retard or minimize infection by the selected virus of an uninfected mammal, e.g., human. Such compositions thus have utility as vaccines. Anti-Tat protein antibodies are not reactive with the HIV-1 proteins used in diagnostic assays to detect seroconversion after infection. Thus, subjects treated with the compositions of this invention would not be stigmatized with false-positive tests for HIV-1 infection, and it would remain possible to detect seroconversion if treated subjects did become infected with HIV-1.

Providing a mammal with the compositions of this invention, whether as a protein/peptide-containing composition or by administration of a novel nucleic acid sequence encoding the immunogen, affords a radically different strategy for AIDS vaccination because it permits the lowering of viral levels by biological interdiction of desirably, greater than about 95%, and preferably greater than about 99%, of known Tat protein variants of HIV-1, lowering multiplication of HIV-1.

The use of the Tat immunogen-containing compositions has a particularly desirable advantage in contrast to other treatments and prophylactic methods employed against such viruses. Because interdiction of the Tat protein extracellularly inhibits the multiplication of all HIV quasi-species or strains indiscriminately, it does not create a selective pressure on the parent virus itself for selection of mutant virus variants. Thus, blocking the uptake of Tat protein by the patient's cells not only reduces the level of viremia, but does so in a manner that precludes the selection of "escape variants".

Additionally, the invention comprises a method of actively treating asymptomatic HIV-1 infected subjects with viremia, since during the course of the disease, extracellular Tat protein likely contributes to the persistent infection and immune abnormalities that are present at this stage of HIV-1 infection. Interdiction of extracellular Tat protein by antibodies induced by immunization according to this invention can reduce viremia with more effective immune control, and result in delay or prevention of progression to AIDS.

The mechanism of the present invention as described above is useful in impeding the course of viral infection and producing desirable clinical results. More specifically, the compositions of this invention are capable of reducing viremia in patients already infected with the virus by blocking further uptake of the Tat protein by uninfected cells. The compositions of the present invention, used either alone or in conjunction with other therapeutic regimens for HIV infected patients, are anticipated to assist in the reduction of viremia and prevention of clinical deterioration.

For such therapeutic uses, the formulations and modes of administration are substantially identical to those described specifically above and may be administered concurrently or simultaneously with other conventional therapeutics for the specific viral infection. For therapeutic use or prophylactic use, repeated dosages of the immunizing compositions may be desirable, such as a yearly booster or a booster at other intervals.

L. Diagnostic Kits of this Invention

The peptides and polypeptides described above can also be employed as reagents of a kit useful for the measurement and detection of titers and specificities of antibodies induced by vaccination with the compositions described above. The kit of the invention can include at least the two required Epitope I peptides identified above, and preferably two or more of the primate-recognized Epitope I and optional immunogens. In one embodiment, each peptide has on its N terminus the protein biotin and a spacer, e.g.,-Ser-Gly-Ser-Gly- [SEQ ID NO: 27]. Alternatively, the peptide may have on its C terminus a spacer, e.g., -Gly-Ser-Gly-Ser- [SEQ ID NO: 25], and the protein biocytin. These embodiments enable the peptides to be bound to an avidin-coated solid support, e.g., a plate or beads. Other binding agents known to those of skill in the diagnostic assay art may also be employed for the same purposes. Also provided in the kit are labeled reagents which detect the binding of antibody to the immobilized Epitope peptides, such as a goat anti-human immunoglobulin or the like. The label on the reagent may be selected from the many known diagnostic labels, such as radioactive compounds, fluorescent compounds and proteins, colorimetric enzymes, etc. The kit thus also contains miscellaneous reagents and apparatus for reading labels, e.g., certain substrates that interact with an enzymatic label to produce a color signal, etc., apparatus for taking blood samples, as well as appropriate vials and other diagnostic assay components. One of skill in the art may also readily select other conventional diagnostic components for this kit.

Such kits and reagents may be employed in a method for detecting the titers and reactivity patterns of antibodies in subjects vaccinated with the compositions of this invention. A method for determining the presence and or titer of antibodies induced by immunization to a Tat immunogen includes the steps of contacting a biological sample from an immunized subject, e.g., a body fluid, preferably blood, serum or plasma, but also possibly urine, saliva and other fluids or tissue, with one or more of the binding sequences of primate-recognized Epitope I and optional immunogens, preferably immobilized on a solid support, such as a plate or beads. The primate-recognized Epitope I and optional binding sequences employed in this method may be the unmodified minimal epitope binding regions.

Once the biological sample is exposed to the immobilized peptides for a sufficient time, the support is washed to eliminate any material from the biological sample which is not bound to the peptides. Such washing steps are conventional in diagnostic assays, and performed with saline. If antibodies to Epitopes I and optional immunogens or a combination thereof, were induced in the subject by the above-described treatment, the immobilized peptides have been bound with antibody from the biological sample. Thereafter, a labeled reagent is added to the material on the support to detect the binding between the peptides on the solid support and antibody in said biological sample. Preferably, such a reagent is an anti-human immunoglobulin, such as goat anti-human immunoglobulin. The label is selected from among a wide array of conventionally employed diagnostic labels, as discussed above. In one embodiment, the label can be a calorimetric enzyme, which upon contact with a substrate produces a detectable color signal. The presence and/or intensity of the color provides evidence of the induction of antibody in the treated subject. This assay may be employed to determine the efficacy of the immunization, as well as to monitor immune status of a patient.

The selection of particular assay steps, as well as a variety of detectable label systems, is well within the skill of the art. Such selection is routine and does not limit the present invention.

M. Advantages of the Invention

One of the advantages of the compositions of this invention is the small number of immunogens required for inclusion into a composition of this invention to cross-react with greater than 95 to greater than 99% of known Tat protein variants of HIV-1 of the common B subtype. As illustrated in the examples below, the primate-recognized Epitope I immunogenic composition containing the two required primate-recognized Epitope I amino acid sequences as well as the six additional Epitope I sequences cross-reacts with 95% Tat proteins of HIV-1 of the common B subtype, as well as with all 56 Tat protein sequences from less frequent non-B subtypes of HIV-1. Thus, a single composition may be usefully employed in protecting against or treating infection, caused by the vast majority of HIV-1 strains that can be encountered.

Further, having identified the precise epitopes of Tat against which binding is desired (i.e., AA5–12 of SEQ ID NO: 15) new desirable Tat peptide immunogens from newly occurring HIV-1 strains or newly discovered strains may be easily identified using the methods described herein, and included in the compositions. This flexibility enables the compositions of this invention to be useful prophylactically against any new strain or strains of HIV-1 identified in the future. In view of the teachings herein, one of skill in the art is expected to be readily able to incorporate new combinations of Tat immunogens (and the nucleic acid constructs encoding them) into the compositions.

For example, the use of conventional techniques such as PCR and high density oligonucleotide arrays [M. J. Kozal et al, *Nature Med*., 2:753 (1996)] enables one of skill in the art to obtain the amino acid sequences of a large array of HIV-1 Tat proteins representing variants of clinical isolates of HIV-1 strains and subtypes. Using such techniques permits determination of other variants of the $^{HIV-}$1 B subtype as well as other subtypes in underdeveloped countries, which have not been so intensively studied to date. The determination of new Tat sequences will enable ready inclusion of the corresponding peptides as immunogens into compositions of this invention, allowing the induction of an antibody response against other rare Tat proteins of HIV-1.

Cross-reactivity studies with antibodies raised to synthetic peptides corresponding to each Tat variant can be utilized to eliminate the need for immunizing with Tat variants in which the sequence changes are immunologically silent, in that these peptides are strongly bound by antibodies to the consensus sequence or other variants.

The following examples illustrate preferred methods for preparing the compositions of the invention and utilizing these compositions to induce antibodies to Tat proteins of the virus in an immunized host. These examples are illustrative only and do not limit the scope of the invention.

EXAMPLE 1—IMMUNOLOGICAL STUDIES ON MINIMAL TAT PROTEIN AMINO ACID SEQUENCES NECESSARY FOR BINDING TO ANTIBODY FOR PRIMATE-RECOGNIZED EPITOPE I IN HIV-1 TAT PROTEIN, SEQUENCE VARIATIONS, AND IMMUNOLOGICAL CROSS-REACTIVITIES OF ANTISERUMS TO THESE SEQUENCES

A. Synthetic Peptide and Conjugates

The synthetic peptides were synthesized by solid phase synthesis on derivatized polyethylene supports [R. M. Valerio et al, *Int. J. Peptide Res*., 44:158–165 (1994)]. Immunizing peptides were synthesized with an amino terminal Cys being incorporated to facilitate coupling to a carrier protein and an amidated C-terminus. Detector peptides were synthesized with an amino terminal biotin-Ser-Gly-Ser-Gly-sequence [SEQ ID NO: 27] and a free acid function at the C-terminus for use in ELISA assays for detection of reactivity and cross-reactivity. Immunizing peptides, covalently conjugated to diphtheria toxoid (DT) carrier protein via the cysteinyl side chain, with a peptide-carrier ratio of 5–8 [A. C. J. Lee et al., *Molec. Immunol*, 17:749 (1980)], were purified by high pressure liquid chromatography (HPLC) to greater than 95% purity by analytical HPLC and mass spectrometry, with detector peptides being used at greater than 50% purity.

B. Immunizations

The peptide conjugates were taken up in purified water and emulsified 1:1 with complete Freund's adjuvant (CFA) or incomplete Freund's adjuvant (IFA) [ANTIBODIES—A LABORATORY MANUAL, Eds. E. Harlow and P. Lane, Cold Spring Harbor Laboratory (1998)]. Total volume per primate was 1 ml, and this contained 100 μg of peptide coupled to DT.

Rhesus monkeys that were part of a viral challenge study were immunized with antigen in IFA/CFA as follows. Several primates were used for the immunizing peptide, with the initial intramuscular (IM) injection with conjugate in CFA and a subsequent IM boost at 2 weeks with conjugate in IFA. A pre-bleed was drawn before the first injection and larger bleeds were taken 3 and 5 weeks after the booster injection.

C. ELISA Titers

ELISA assays were performed as described by H. M. Geysen et al., *Proc. Natl. Acad. Sci. USA*, 81:3998 (1983). Antibody titer was the reciprocal of the serum dilution that resulted in an absorbence 1.0 OD units above background. The geometric mean titer (GMT) for 2–3 serums was calculated for each response, or single serums only were available for some monkey immunizations.

Figure 1B:
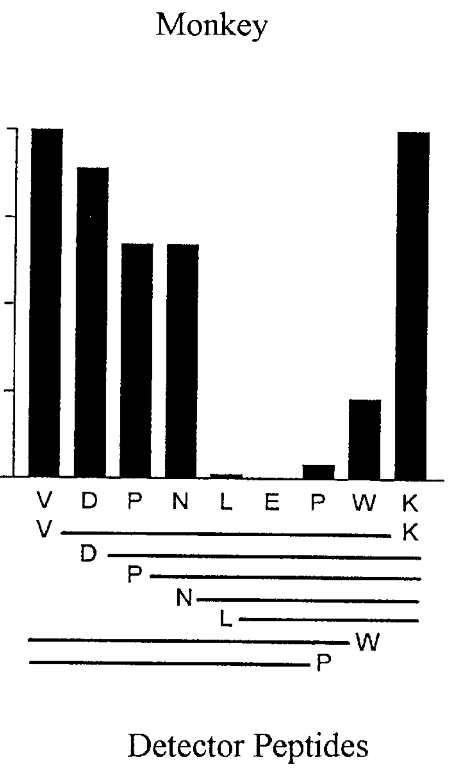
FIG. 1B is a graph of ELISA titers of primate antiserum to larger linear Epitope I peptides on truncated detector peptides, expressed as a percentage of maximal binding to larger peptides. The N- or C-terminal amino acids of the corresponding detector peptides are shown below each column in single letter code.

ELISA results for this assay in rabbits vs. monkeys are shown in FIGS. 1A and 1B, respectively. The ELISA results demonstrated that the primate antibodies to the immunogen incorporating Epitope I were reacting with the sequence -Asp-Pro-$Arg_7$-Leu-$Glu_9$-Pro-Trp-$Lys_{12}$- [AA5–12 of SEQ ID NO: 15]. As discussed below, the positions 7, 9 and 12 represent common variants of this Epitope I peptide recognized by primates.

D. Analysis of Amino Acid Sequence Diversity Within the Epitopes

HIV-1 Tat first exon sequences were retrieved from GenBank and the Los Alamos Human Retroviruses and AIDS databases [HUMAN RETROVIRUSES and AIDS 1996, published by the Theoretical Biology and Biophysics Group of the Los Alamos National Laboratory, Los Alamos, NM, and additional sequences kindly obtained from GenBank by Esther Guzman of the Los Alamos Laboratory]. Incomplete sequences and sequences with stop codons or base deletions leading to a frameshift were deleted, as were obviously identical repeat sequences from the same isolation. Variations of amino acids at the positions within the epitopes were recorded and tabulated.

E. Antigenic Cross-Reactivities Between Variants

Antisera to the epitope consensus sequence were titered by ELISA on the consensus sequence and on sequences with common amino acid variants to determine the effects of amino acid polymorphisms on antigenicity.

F. Variations in Sequences

The primate-recognized Epitope I consensus sequences were evaluated for maximal frequency and recognition by primate antibodies. The antigenic and sequence conservation in HIV-I Tat proteins from 294 HIV-1 Tat proteins from 294 B lade (I) viruses and 56 non-B lade (II) viruses were evaluated for the epitopes and the results tabulated in Tables II through VI below.

The top row of Tables II and III indicates the consensus sequence for maximal frequency. The middle rows contain the percent incidence of amino acids found in greater than 5% of sequences at each position, if multiple. The bottom row of each table is the total incidence including amino acids occurring in greater than 5% of sequences, if multiple. All of these selections in Table II create antigenically distinct epitopes (<25% cross-reactivity); and all of the selections in Table III, except for the entries under amino acid 4.

TABLE II

Epitope I - 294 B clades

| $Val_4$ | $Asp_5$ | $Pro_6$ | $Arg_7$ | $Leu_8$ | $Glu_9$ | $Pro_{10}$ | $Trp_{11}$ | $Lys_{12}$ |
|---|---|---|---|---|---|---|---|---|
| | | | Arg (73) | | | | | Lys (96) |
| | | | Lys (12) | | | | | Asn (2) |
| | | | Ser (11) | | | | | |
| | | | Asn (4) | | | | | |
| 100% | 98% | 100% | 100% | 100% | 100% | 100% | 100% | 100% |

TABLE III

Epitope I - 56 Non B clades

| $Val_4$ | $Asp_5$ | $Pro_6$ | $Asn_7$ | $Leu_8$ | $Glu_9$ | $Pro_{10}$ | $Trp_{11}$ | $Asn_{12}$ |
|---|---|---|---|---|---|---|---|---|
| Val (89) | | | Asn (79) | | Glu (86) | | | Asn (87) |
| Ile (11) | | | Lys (14) | | Asp (14) | | | Lys (13) |
| | | | Ser(5) | | | | | |
| 100% | 100% | 100% | 98% | 96% | 100% | 98% | 100% | 100% |

As shown in Tables II and III, primate-recognized Epitope I has a potential 16-fold antigenic polymorphism, but one major antigen exists for the B clades and another major antigen exists for the non-B clades. Five other variants account for greater than 95% of known Tat variants. See Tables IV and V; sequences indicated with an asterisk are represented in both B and non-B clades. Table IV—B Clades (294 sequences).

TABLE IV

B Clades (294 sequences)

| Primate epitope sequence | SEQ ID NOs | Incidence | Percent Incidence |
|---|---|---|---|
| ValAspProArgLeuGluProTrpLys | AA4-12 of SEQ ID NO: 15 | 220 | 75 |
| ValAspProLysLeuGluProTrpLys* | AA185-193 of SEQ ID NO: 12 | 35 | 12 |
| ValAspProSerLeuGluProTrpLys | AA120-127 of SEQ ID NO: 12 | 20 | 7 |
| ValAspProAsnLeuGluProTrpLys* | AA55-63 of SEQ ID NO: 12 | 7 | 2 |
| | | Total: 282 | Total: 96 |
| ValAspProArgLeuGluProTrpAsn | 28 | 1 | <1 |

TABLE V

| Non-B Clades (56 sequences) | | | |
|---|---|---|---|
| Primate epitope sequence | SEQ ID NOs | Incidence | Percent Incidence |
| ValAspProAsnLeuGluProTrpAsn | AA227-235 of SEQ ID NO: 13 | 36 | 64 |
| ValAspProLysLeuGluProTrpAsn | AA344-352 of SEQ ID NO: 13 | 8 | 14 |
| ValAspProAsriLeuAspProTrpAsn | 29 | 6 | 11 |
| ValAspProAsnLeuGluProTrpLys* | AA55-63 of SEQ ID NO:13 | 3 | 5 |
| ValAspProLysLeuGluProTrpLys* | AA185-193 of SEQ ID NO:12 | 1 | 2 |
| | | Total: 53 | Total: 95 |
| ValAspProSerLeuGluProTrpAsn | AA279-287 of SEQ ID NO: 13 | 1 | 2 |
| ValAspProSerLeuAspProTrpAsn | 30 | 1 | 2 |
| ValAspProAsnLeuAspProTrpLys | 31 | 1 | 2 |

Table VI shows the poor antigenic cross-reactivity of the position 7 variants of Epitope I, the antigenic distinction of the position 9 variants and the extreme lack of cross-reactivity of antisera to GluProValAspProAsn$_7$LeuGlu$_9$ProTrpAsn$_{12}$ [AA225–235 of SEQ ID NO: 13] with GluProValAspProArg$_7$LeuGlu$_9$ProTrpLys$_{12}$ [AA 2–12 of SEQ ID NO: 15] containing variants at both positions 7 and 12. It further shows antigenic distinction of Glu9 and Asp9 variants.

TABLE VI

ELISA Reactivity of monkey antiserums to Epitope I Immunogens on Detector peptides with Tat amino acid positions 7, 9 and 12 Variations

| Immunogen epitope sequence | Detector peptide epitope sequence Titer (% of titer of self peptide) | | | |
|---|---|---|---|---|
| GluProVal AspPro**Asn**$_7$ LeuGlu$_9$Pro TrpLys$_{12}$ [AA53-63 of SEQ ID NO: 12] | GluProVal AspPro**Asn**$_7$ LeuGlu$_9$Pro TrpLys12 [AA53–63 of SEQ ID NO: 12] 119,000 (100) | GluProVal AspPro**Arg**$_7$ LeuGlu$_9$Pro TrpLys$_{12}$ [AA2–12 of SEQ ID NO: 15] 25,000 (21) | GluProVal AspPro**Lys**$_7$ LeuGlu$_9$Pro TrpLys$_{12}$ [AA183–193 of SEQ ID NO: 12] 24,000 (20) | GluProVal AspPro**Ser**$_7$ LeuGlu$_9$Pro TrpLys$_{12}$ [AA105–115 of SEQ ID NO: 12] 24,000 (20) |
| GluProVal AspPro**Asn**$_7$ LeuGlu$_9$Pro Trp**Asn**$_{12}$ [AA225-235 of SEQ ID NO: 13] | GluProVal AspPro**Asn**$_7$ LeuGlu$_9$Pro Trp**Asn**$_{12}$ [AA225-235 of SEQ ID NO: 13] 157,000(100) | GluProVal AspPro**Asn**$_7$ LeuGlu$_9$Pro TrpLys$_{12}$ [AA53-63 of SEQ ID NO: 12] 23,000(15) | GluProVal AspPro**Arg**$_7$ LeuGlu$_9$Pro TrpLys$_{12}$ [AA2-12 of SEQ ID NO: 15] 2000(1) | |
| GluProVal AspPro**Asn** Leu**Glu**$_9$Pro TrpLys$_{12}$ [AA53-63 of SEQ ID NO: 12] | GluProVal AspPro**Asn**$_7$ Leu**Glu**$_9$Pro TrpLys$_{12}$ [AA53-63 of SEQ ID NO: 12] 163,000 (100) | GluProVal AspPro**Asn**$_7$ Leu**Asp**$_9$Pro TrpLys$_{12}$ [SEQ ID NO: 32] 6000 (4) | | |

EXAMPLE 2—IMMUNOLOGICAL STUDIES ON MINIMAL TAT PROTEIN AMINO ACID SEQUENCES NECESSARY FOR BINDING TO ANTIBODY FOR PRIMATE-RECOGNIZED EPITOPE II IN HIV-1 TAT PROTEIN, SEQUENCE VARIATIONS, AND IMMUNOLOGICAL CROSS-REACTIVITIES OF ANTISERUMS TO THESE SEQUENCES

Using the same procedures outlined in Example 1, the incidence of amino acid sequence variation for 294 B clade and 56 non-B clade HIV-1 Tat sequences was determined within the Epitope II boundaries of antibody binding in monkeys. The results are reported in Tables VII and VIII. The top lines of the tables contain the consensus sequence. The middle lines contain the percent incidence of amino acids found in greater than 5% of sequences at each position, if multiple. The bottom line shows the total incidence including amino acids occurring in greater than 5% of sequences, if multiple. The amino acid variants at Tat position 42 were antigenically cross-reactive.

TABLE VII

| Epitope II- 294 B clades | | | | | | | | | |
|---|---|---|---|---|---|---|---|---|---|
| $Lys_{41}$ | $Gly_{42}$ | $Leu_{43}$ | $Gly_{44}$ | $Ile_{45}$ | $Ser_{46}$ | $Tyr_{47}$ | $Gly_{48}$ | $Arg_{49}$ | $Lys_{50}$ |
| | Gly (72) Ala (28) | | | | | | | | |
| 100% | 100% | 99% | 99% | 100% | 98% | 99% | 100% | 99% | 100% |

TABLE VIII

| Epitope II- 56 Non-B clades | | | | | | | | | |
|---|---|---|---|---|---|---|---|---|---|
| $Lys_{41}$ | $Gly_{42}$ | $Leu_{43}$ | $Gly_{44}$ | $Ile_{45}$ | $Ser_{46}$ | $Tyr_{47}$ | $Gly_{48}$ | $Arg_{49}$ | $Lys_{50}$ |
| 100% | 100% | 100% | 99% | 100% | 95% | 100% | 100% | 98% | 100% |

As revealed in Tables VII and VIII, Epitope II shows almost complete antigenic conservation.

Figures 2A, 2B:
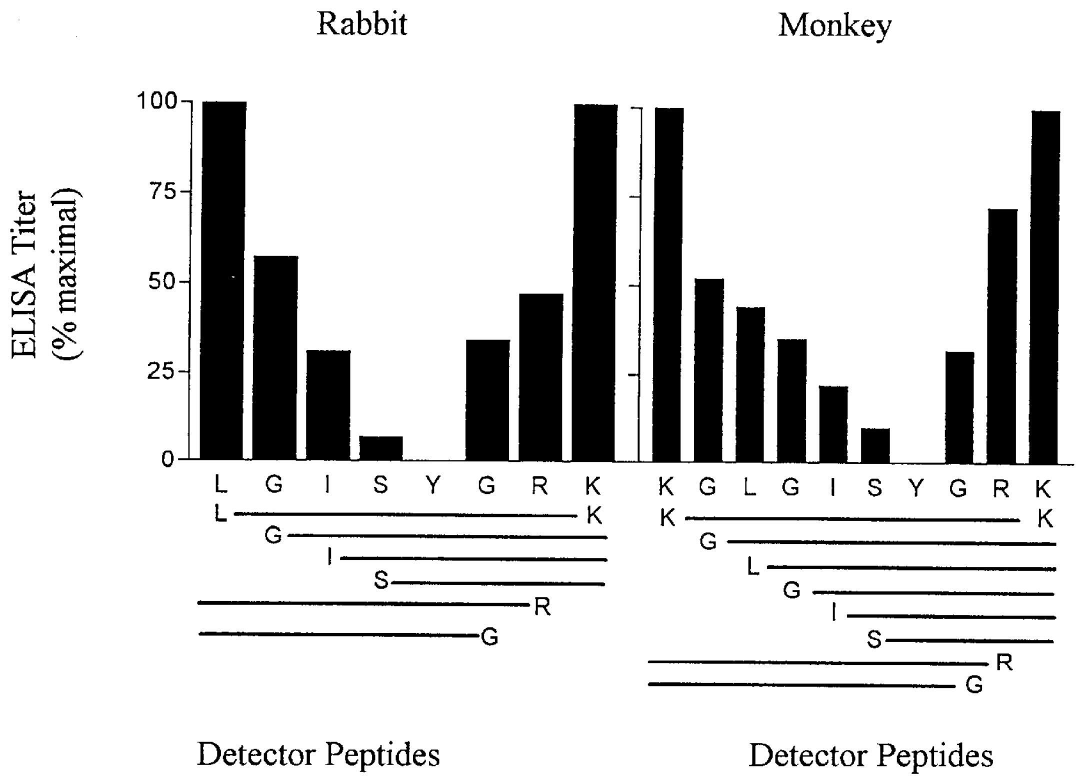
FIG. 2A is a graph of ELISA titers of rabbit antiserum to linear Epitope II peptides on truncated detector peptides, expressed as a percentage of maximal binding to larger peptides. The N- or C-terminal amino acids of the corresponding detector peptides are shown below each column in single letter code.
FIG. 2B is a graph of ELISA titers of primate antiserum to larger linear Epitope II peptides on truncated detector peptides, expressed as a percentage of maximal binding to larger peptides. The N- or C-terminal amino acids of the corresponding detector peptides are shown below each column in single letter code.

ELISA reactivity of monkey antiserums to Epitope II immunogen on detector peptides with Tat $Gly_{42}$ or $Ala_{42}$ (variant) within the detector sequences were measured and reported in Table IX below. See FIGS. 2A and 2B for a graphical comparison of results in rabbits vs. monkeys, respectively.

TABLE IX

| Immunogen epitope sequence | Detector peptide epitope sequence Titer (% of titer on self peptide) | |
|---|---|---|
| LysGlyLeuGlyIle SerTyrGlyArgLys [AA41–50 of SEQ ID NO: 15] | LysGlyLeuGlyIleSerTyr GlyArgLys [AA41–50 of SEQ ID NO: 15] 25,000 (100%) | LysAlaLeuGlyIleSerTyr GlyArgLys [SEQ ID NO:33] 19,000 (76%) |

EXAMPLE 3—DEVELOPMENT OF HUMAN MONO CLONAL ANTIBODY TREATMENT FOR ASYMPTOMATIC HIV-1 INFECTIONS

Commercially available antibody humanized mice are immunized with a suitable amount of the Epitope II immunogen: Cys-Gly-Ser-Lys-Gly-Leu-Gly-Ile-Ser-Tyr-Gly-Arg-Lys-amide [SEQ ID NO:34] coupled to diphtheria toxoid carrier protein. Hybridomas are screened on biotin-Ser-Gly-Ser-Gly-Leu-Gly-Ile-Ser-Tyr-Gly-Arg-Lys-OH [SEQ ID NO: 35] on streptavidin-coated plates, and an IgG monoclonal antibody with subnanomolar binding affinity and no binding to complement receptors is selected. Specificity is confirmed on recombinant HIV-1 Tat protein.

Since the monoclonal antibody is directed to a non-self antigen, a conventional pre-clinical production, purification and safety testing is anticipated. Human monoclonal antibodies have a half-life of 20 days in man vs. the 18 hours half-life of OKT3, a mouse monoclonal antibody which is extensively consumed on internal CD3. Daily doses of 5 mg OKT3 maintain trough levels around 1 microgram/ml in man. Thus, a biweekly dose of 5 mg anti-Tat monoclonal antibody is anticipated to be sufficient to maintain similar trough levels, a greater than fifty-fold molar excess over the estimated maximal circulating levels of up to 1 ng/ml for HIV-1 Tat protein in infected subjects.

Control of plasma viral loads is now an accepted criterion of efficacy for HIV-1 treatment. The efficacy of an anti-Tat monoclonal antibody can be rapidly determined in asymptomatic HIV-1 infected subjects, initially with a four week course of treatment. This protocol is useful in untreated patients, in patients that have failed in HAART protocols for various reasons, or in patients controlled by HAART therapy, with withdrawal of this therapy for 4 weeks (viral loads rebound rapidly if HAART is stopped). A 2 to 3 log reduction in plasma viral loads to below the LOD (50 viral RNA copies/mL) supports monotherapy with the monoclonal antibody, which is evaluated over a longer time-span. Reduction over one log (90%), but not below the LOD suggests the use of the monoclonal antibody as a component in therapy.

EXAMPLE 4—DEVELOPMENT OF A UNIVERSAL VACCINE TO PREVENT PROGRESSION TO AIDS IN SUBJECTS

A. Construction of a Synthetic Gene

FIG. 3A illustrates a synthetic gene encoding four copies each of the four polymorphs of Epitope I detected for the rabbit antibody response, plus four copies of Epitope II, expressed in *E. coli* as a linear fusion protein with *E. coli* DnaK (HSP70). This expressed protein contained all the antigenic epitopes when tested in ELISA with epitope specific rabbit antiserums. However, when used to immunized in rabbit or monkey, all Epitope I variants were immunogenic, but Epitope II was not. Thus, Epitope II is best used as a synthetic peptide conjugate coupled to an appropriate carrier protein.

FIG. 3B illustrates a novel octavalent synthetic gene constructed to incorporate in frame eight primate-recognized Epitope I polymorphs, based on the polymorphism within the Epitope I boundaries recognized in primates:

R1-Asp-Pro-Arg-Leu-Glu-Pro-Trp-Lys-R2 [SEQ ID NO: 17]

R1-Asp-Pro-Lys-Leu-Glu-Pro-Trp-Lys-R2 [SEQ ID NO: 19]

R1-Asp-Pro-Lys-Leu-Glu-Pro-Trp-Asn-R2 [SEQ ID NO: 22]

R1-Asp-Pro-Ser-Leu-Glu-Pro-Trp-Lys-R2 [SEQ ID NO: 20]

R1-Asp-Pro-Ser-Leu-Glu-Pro-Trp-Asn-R2 [SEQ ID NO: 24]

R1-Asp-Pro-Asn-Leu-Glu-Pro-Trp-Lys-R2 [SEQ ID NO: 21]

R1-Asp-Pro-Asn-Leu-Glu-Pro-Trp-Asn-R2 [SEQ ID NO: 18] and

R1-Asp-Pro-Asn-Leu-Asp-Pro-Trp-Asn-R2 [SEQ ID NO: 23]

The Epitope I sequences are separated by dipeptide spacers containing Gly and/or Ser residues. The gene is assembled as described in W. P. C. Stemmer et al., *Gene*, 164:49 (1995). Briefly, top strand 60-mer oligonucleotides (oligos) and bottom strand oligos with 20 nucleotide (nt) overlaps are synthesized along with two end 50-mers. The 60-mers are incubated together under hybridizing conditions and polymerase chain reaction (PCR) is used to fill in the sequence and amplify it. The end 50-mers are then added and the assembly completed by PCR, with isolation of the full length gene on agarose gel. The gene is sequenced and found to have the correct sequence within the actual epitopes. A similar heptavalent gene may be constructed by eliminating the rare variant R1-Asp-Pro-Ser-Leu-Glu-Pro-Trp-Asn-R2 [SEQ ID NO: 24].

B. Expression of the Fusion Protein

This gene described above is then excised with restriction enzymes and inserted into a suitable expression vector containing, in frame, the sequence for diphtheria toxoid (HSP70). *E. coli* are transfected and colonies expressing the protein are isolated. The isolated colonies are grown and expression is induced. Protein from colonies expressing the fusion protein are identified. The resulting protein is purified utilizing conventional methods.

FIG. 3C illustrates a monovalent Epitope II immunogen optionally prepared as a conjugate of synthetic peptide with a carrier protein such as diphtheria toxoid, using similar techniques.

C. Assays for Assessing the Expression of the Epitopes Correctly in the Fusion Protein and Efficacy in Inducing Anti-Tat Antibodies Four variants of Epitopes I, in which $Y_7$ is either Arg, Asn, Lys or Ser, and $X_9$ is Glu and $Z_{12}$ is Lys, and both variants of Epitope II are constructed in a synthetic gene and expressed as a fusion protein, as described in paragraphs A and B above. To determine if each epitope is expressed in the fusion protein in a form that can be recognized by primate antisera, primate antiserums generated to synthetic peptides corresponding to the Epitope I sequences are tested by ELISA, using conventional methodology. Plates are initially directly coated with the fusion protein and then exposed to 100 $\mu$g/ml solution of antiserums (e.g., rabbit antisera) which are known to be reactive for Epitopes I and II. The variant epitope sequences are expressed in a conformation recognizable by antibodies to the corresponding synthetic peptides, as shown by a titer of greater than 32,000 for each epitope.

To evaluate the immunogenicity of the multivalent immunogen, monkeys were immunized with the fusion protein in IFA. The monkey antisera was then assessed on synthetic peptides of the Epitopes I and II. Significant titers developed to the Epitope I variants, i.e., titer of 28,000 to Epitope I, when $Y_7$ is Arg and $Z_{12}$ is Lys; titer of 16,000 to Epitope I when $Y_7$ is Asn and $Z_{12}$ is Lys; titer of 37,000 to Epitope I, when $Y_7$ is Lys and $Z_{12}$ is Lys; and titer of 4,000 to Epitope I, when $Y_7$ is Ser and $Z_{12}$ is Lys. Titer to Epitope II was 700, indicating that this epitope is best presented for immunization as a synthetic peptide coupled to a carrier.

EXAMPLE 5: METHOD AND KITS FOR DETECTING TITERS AND SPECIFICITIES OF ANTIBODIES INDUCED BY VACCINATION

To follow the titer and specificities of antibodies induced following immunization with the vaccines of this invention, an assay method may be employed. In one embodiment of such as assay, peptides containing the primate-recognized Epitope I sequences reported in Example 1 (depending on the composition of the immunizing vaccine) are used to develop kits measuring titers and reactivity patterns of antibodies in vaccinated subjects.

These peptides are synthesized with Biotin-Ser-Gly-Ser-Gly- [SEQ ID NO:36] at the N-terminus. Each peptide is coated onto separate avidin coated plates, with a sequence -Ser-Gly-Ser-Gly- [SEQ ID NO:27] serving as a spacer to ensure that the relevant peptide sequence is external to the biotin binding pocket of avidin. The plates are then incubated with dilutions of test serum, washed, and the antibody binding determined with reagent to human immunoglobulin, e.g., goat anti-human immunoglobulin, directly labeled with enzyme. A reagent is employed to react with the enzyme and produce a calorimetric signal (R&D kit inserts).

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A composition comprising a peptide or polypeptide of the formula R1-Asp-Pro-Asn-Leu-Asp-Pro-Trp-Asn-R2 SEQ ID NO: 8, wherein R1 is selected from the group consisting of hydrogen, a lower alkyl, a lower alkanoyl, and a sequence of between 1 to about 5 amino acids, optionally substituted with a lower alkyl or lower alkanoyl; and wherein R2 is selected from the group consisting of a free hydroxyl, an amide, and a sequence of one or up to about 5 additional amino acids, optionally substituted with an amide.

2. The composition according to claim 1 wherein R1 is Val, resulting in the sequence Val-Asp-Pro-Asn-Leu-Asp-Pro-Trp-Asn of SEQ ID NO: 8.

3. The composition according to claim 1 wherein R1 is $X_2$-Pro-Val, wherein $X_2$ is selected from the group consisting of Glu and Asp, optionally substituted with a lower alkyl or lower alkanoyl, resulting in the sequence $X_2$-Pro-Val-Asp-Pro-Asn-Leu-Asp-Pro-Trp-Asn SEQ ID NO: 38.

4. The composition according to claim 1 wherein R2 is -His-Pro-Gly-Ser-, resulting in the sequence Val-Asp-Pro-Asn-Leu-Asp-Pro-Trp-Asn-His-Pro-Gly-Ser SEQ ID NO:16, wherein said carboxy-terminal Ser is optionally substituted with an amide.

5. The composition according to claim 1 wherein said peptides or polypeptides are produced synthetically.

6. The composition according to claim 1 wherein said peptides or polypeptides are produced recombinantly.

7. The composition according to claim 1 wherein one or more of said peptides is expressed as a synthetic peptide coupled to a carrier protein.

8. The composition according to claim 1 wherein one or more of said peptides is expressed as a multiple antigenic peptide, optionally coupled to a carrier protein.

9. The composition according to claim 1 wherein one or more of the selected peptides is expressed within a recombinantly produced protein, optionally fused in frame with a carrier protein.

10. The composition according to any of claims 7–9, wherein said carrier protein is selected from the group consisting of an *E. coli* DnaK protein, a GST protein, a mycobacterial heat shock protein 70, a diphtheria toxoid, a tetanus toxoid, a galactokinase, an ubiquitin, an α-mating factor, a β-galactosidase, and an influenza NS-1 protein.

11. A pharmaceutical composition comprising a composition of claim 1, a pharmaceutically acceptable carrier and an optional adjuvant.

12. The composition according to claim 1, further comprising at least two variants of a peptide or polypeptide of the formula selected from the group consisting of:

R1-Asp-Pro-$Y_7$-Leu-Glu-Pro-Trp-$Z_{12}$-R2 SEQ ID NO: 8, wherein $Y_7$ is selected from the group consisting of Arg, Lys, Ser and Asn;

wherein $Z_{12}$ is selected from the group consisting of Lys and Asn;

wherein R1 is selected from the group consisting of hydrogen, a lower alky, a lower alkanoyl, and a sequence of between 1 to about 5 amino acids, optionally substituted with a lower alkyl or lower alkanoyl; and wherein R2 is selected from the group consisting of a free hydroxyl, an amide, and a sequence of one or up to about 5 additional amino acids, optionally substituted with an amide, and wherein at least one said variant is R1-Asp-Pro-Arg-Leu-Glu-Pro-Trp-Lys-R2 SEQ ID NO: 17, and the other said variant is R1-Asp-Pro-Asn-Leu-Glu-Pro-Trp-Asn-R2 SEQ ID NO: 18.

13. The composition according to claim 12, further comprising a peptide in which R1 is Val.

14. The composition according to claim 12, further comprising a peptide in which R1 is $X_2$-Pro-Val, wherein $X_2$ is selected from the group consisting of Glu and Asp, optionally substituted with a lower alkyl or lower alkanoyl.

15. The composition according to claim 12 further comprising a peptide wherein R2 is -His-Pro-Gly-Ser-, wherein said carboxy-terminal Ser is optionally substituted with an amide.

16. The composition according to claim 12 comprising one or more additional sequences selected from the group consisting of:

R1-Asp-Pro-Lys-Leu-Glu-Pro-Trp-Lys-R2 SEQ ID NO: 19

R1-Asp-Pro-Lys-Leu-Glu-Pro-Trp-Asn-R2 SEQ ID NO: 22

R1-Asp-Pro-Ser-Leu-Glu-Pro-Trp-Lys-R2 SEQ ID NO: 20

R1-Asp-Pro-Ser-Leu-Glu-Pro-Trp-Asn-R2 SEQ ID NO: 24 and

R1-Asp-Pro-Asn-Leu-Glu-Pro-Trp-Lys-R2 SEQ ID NO: 21, wherein R1 is selected from the group consisting of hydrogen, a lower alkyl, a lower alkanoyl, and a sequence of between 1 to about 5 amino acids, optionally substituted with a lower alkyl or lower alkanoyl; and wherein R2 is selected from the group consisting of a free hydroxyl, an amide, and a sequence of one or up to about 5 additional amino acids, optionally substituted with an amide.

17. The composition according to claim 16, further comprising at least seven of said amino acid sequences.

* * * * *

UNITED STATES PATENT AND TRADEMARK OFFICE

CERTIFICATE OF CORRECTION

PATENT NO. : 6,399,067 B1
DATED : June 4, 2002

INVENTOR(S) : Gideon Goldstein

It is certified that error appears in the above-identified patent and that said Letters Patent is hereby corrected as shown below:

<u>Column 2,</u>
Line 12, replace “WO95/3 1999,” with -- WO95/31999 --.

<u>Column 23,</u>
Line 61, replace “$^{HIV-}$1” with -- HIV-1 --.

<u>Column 25,</u>
Line 34, replace “294 B lade (I) viruses and 56 non-B lade (II)” with
-- 294 B clade (I) viruses and 56 non-B clade (II) --.

<u>Column 27,</u>
Line 15, Table V, replace “ValAspProAsriLeuAspProTrpAsn” with
-- ValAspProAsnLeuAspProTrpAsn --.
Line 46, replace “TrpLys12” with -- TrpLys$_{12}$ --.

<u>Column 32,</u>
Line 35, replace “calorimetric” with -- colorimetric --.

Signed and Sealed this

Twenty-first Day of January, 2003

JAMES E. ROGAN
*Director of the United States Patent and Trademark Office*